(12) United States Patent
Lindeman et al.

(10) Patent No.: US 10,492,394 B2
(45) Date of Patent: Dec. 3, 2019

(54) RED-YELLOW STRIPED PEPPERS

(71) Applicant: Enza Zaden Beheer B.V., Enkhuizen (NL)

(72) Inventors: Wouter Lindeman, Woerden (NL); Robin Paul Huibers, Wijk bij Duurstede (NL); Simon Aigner, Enkhuizen (NL); Chami Kim, Antibes (FR)

(73) Assignee: Enza Zaden Beheer B.V., Enkhuizen (NL)

( * ) Notice: Subject to any disclaimer, the term of this patent is extended or adjusted under 35 U.S.C. 154(b) by 156 days.

(21) Appl. No.: 15/493,000

(22) Filed: Apr. 20, 2017

(65) Prior Publication Data

US 2017/0223915 A1    Aug. 10, 2017

Related U.S. Application Data

(63) Continuation-in-part of application No. 14/121,903, filed on Oct. 30, 2014, now Pat. No. Plant 28,123.

(60) Provisional application No. 61/899,010, filed on Nov. 1, 2013, provisional application No. 62/366,927, filed on Jul. 26, 2016, provisional application No. 62/326,619, filed on Apr. 22, 2016.

(51) Int. Cl.
| | |
|---|---|
| *A01H 1/04* | (2006.01) |
| *C12Q 1/6895* | (2018.01) |
| *A01H 5/08* | (2018.01) |
| *A01H 1/02* | (2006.01) |
| *A01H 4/00* | (2006.01) |

(52) U.S. Cl.
CPC ............... *A01H 5/08* (2013.01); *A01H 1/02* (2013.01); *A01H 4/008* (2013.01); *C12Q 1/6895* (2013.01); *A01H 1/04* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 5,262,316 | A | 11/1993 | Engler et al. |
| 5,523,520 | A | 6/1996 | Hunsperger et al. |
| 5,959,186 | A | 9/1999 | Arevalos et al. |
| 6,124,528 | A | 9/2000 | Shewmaker |
| 6,498,287 | B2 | 12/2002 | Nash |
| 7,642,423 | B2 | 1/2010 | Nicolet et al. |
| 8,013,222 | B2 | 9/2011 | McCarthy |
| 8,022,278 | B2 | 9/2011 | Lindeman et al. |
| 8,026,424 | B2 | 9/2011 | Van Der Heiden |
| 8,044,273 | B2 | 10/2011 | Van Der Heiden |
| 8,067,681 | B2 | 11/2011 | Van Der Heiden |
| 8,338,672 | B2 | 12/2012 | Lindeman |
| 8,415,536 | B2 | 4/2013 | Leij |
| 8,536,419 | B2 | 9/2013 | Lindeman |
| 8,618,370 | B2 | 12/2013 | Lindeman et al. |
| 8,816,170 | B2 | 8/2014 | Aardse |
| 9,089,099 | B2 | 7/2015 | Sances Lopez |
| 9,192,113 | B2 | 11/2015 | Lindeman |
| 9,301,464 | B2 | 4/2016 | Sances Lopez |
| 9,320,215 | B2 | 4/2016 | Lindeman et al. |
| 9,474,220 | B2 | 10/2016 | Van Der Heiden |
| 9,572,313 | B2 | 2/2017 | Sances Lopez |
| PP28,123 | P3 * | 6/2017 | Lindeman ............... A01H 5/08 |
| 9,832,946 | B2 | 12/2017 | Tarekegn |
| 10,051,829 | B2 | 8/2018 | Lindeman |
| PP29,897 | P3 * | 11/2018 | Lindeman ............... A01H 5/08 |
| 2006/0059585 | A1 | 3/2006 | Jankowski et al. |
| 2006/0195921 | A1 | 8/2006 | Van Der Heiden |
| 2014/0289885 | A1 | 9/2014 | Van Der Heiden |
| 2015/0128320 | P1 * | 5/2015 | Lindeman ............... A01H 5/08 |
| 2015/0327458 | A1 | 11/2015 | Bouw |
| 2016/0302371 | A1 | 10/2016 | Tarekegn |
| 2017/0196179 | A1 | 7/2017 | Lindeman |
| 2018/0035590 | P1 * | 2/2018 | Lindeman |
| 2018/0042153 | P1 | 2/2018 | Lindeman |
| 2018/0042195 | A1 | 2/2018 | Lindeman |
| 2018/0049385 | A1 | 2/2018 | Tarekegn |
| 2019/0110386 | P1 | 4/2019 | Lindeman |
| 2019/0166787 | A1 | 6/2019 | Lindeman |

FOREIGN PATENT DOCUMENTS

| | | |
|---|---|---|
| WO | 2001/062075 A2 | 8/2001 |
| WO | 2011/003471 A1 | 1/2011 |

OTHER PUBLICATIONS

"Carmen Italian Sweet Pepper", uploaded from Bonnie Plants website, 2006, 1 page.
Chae et al., "Development of Resistant Pepper Lines against Anthracnose using Interspecific Crossing Baccatum and C. Annuum", Capsicum and Eggplant Newsletter, vol. 22, 2003, pp. 121-124.
CPVR 2009/2170. Sweet 46, Filed Oct. 23, 2009, Granted Apr. 23, 2012, 7 pages.
"Database WPI, Section Ch, Week 20327", Derwent Publications Ltd., Antal, J., 'Kurtovszka Kapia' Capsicum Annum, Jan. 28, 2003, 1 page.

(Continued)

*Primary Examiner* — Bratislav Stankovic
(74) *Attorney, Agent, or Firm* — Morrison & Foerster LLP

(57) ABSTRACT

Certain aspects of the present disclosure relate to chimeric pepper plants that produce pepper fruit having a yellow and red striped color, and to seeds that produce the chimeric pepper plants. Other aspects of the present disclosure relate to methods of generating and selecting chimeric pepper plants that produce pepper fruit having a yellow and red striped color, as well as methods of limiting propagation of off-type pepper plant progeny that produce pepper fruit of a single color.

9 Claims, 8 Drawing Sheets

(8 of 8 Drawing Sheet(s) Filed in Color)

Specification includes a Sequence Listing.

(56) References Cited

OTHER PUBLICATIONS

Enza Zaden Beheer B.V., "Database: Netherlands—Application Date: Applications for Plant Breeder's Rights, Application No. PPS1238 'E490264'", Jan. 27, 2011, 2 pages. (See Communication under 37 CFR § 1.98(a) (3)).

Enza Zaden Beheer B.V., Official Gazette of the Community Plant Variety Office; 2010/6; Publication Notice for Application No. CPVR 20101771 'Capsicum annuum L.', Dec. 15, 2010, 3 pages. (See Communication under 37 CFR § 1.98(a) (3)).

Enza Zaden Beheer B.V., "PBR 5210 ('Healey')", Crop Reports, Available at <http://www.inspection.gc.ca/english/plaveg/pbrpov/cropreport/pep/app00008525e.shtml>, filed on Oct. 6, 2010, Granted Mar. 4, 2016, pp. 1-4.

Enza Zaden Beheer B.V., "PVR 20110207 ('Maranello')", filed on Jan. 31, 2011, Granted Mar. 18, 2013, pp. 1-6.

Enza Zaden Beheer B.V., "PVR 20132113 ('Maduro')", filed on Aug. 15, 2013, Granted Jan. 26, 2015, pp. 1-6.

Eshed et al., "Less-Than-Additive Epistatic Interactions of Quantitative Trait Loci in Tomato", Genetics, vol. 143, Aug. 1996, pp. 1807-1817.

Heidmann, Iris, "Applied and Fundamental Aspects of BABY BOOM-mediated Regeneration", Thesis Wageningen University, Oct. 27, 2015, 180 pages.

Heidmann et al., "Efficient Sweet Pepper Transformation Mediated by the BABY BOOM Transcription Factor", Plant Cell Rep, vol. 30, 2011, pp. 1107-1115.

Honma, S, "PI 586678", Capsicum Annuum—MIGOLD, 1986, 4 pages.

Jenkins, Merle T., "The Segregation of Genes Affecting Yield of Grain in Maize", Journal of the American Society of Agronomy, vol. 32, 1940, pp. 55-63.

Kraft et al., "Linkage Disequilibrium and Fingerprinting in Sugar Beet", Theor. Appl. Genet., vol. 101, 2000, pp. 323-326.

Lefebvre et al., "The Capsanthin-Capsorubin Synthase Gene: A Candidate Gene for they Locus Controlling the Red Fruit Colour in Pepper", Plant Molecular Biology, vol. 36, 1998, pp. 785-789.

Lindeman et al., "U.S. Appl. No. 15/732,241, filed Oct. 11, 2017, titled "Pepper Plant Named YY5"".

Molchova et al., "On the Interspecific Crossability Between *Capsicum annuum* L. and *Capsicum pubescens* R. & P.; *Capsicum annuum* L. And Capsicum Pendulum Wild. (SIN BACCATUM)", Capsicum Newsletter, vol. 1, 1982, pp. 39-41.

Murashige et al., "A Revised Meditnn for Rapid Growth and Bio Assays with Tobacco Tissue Cultures", Physiologia Plantarum, Vo. 15, 1962, pp. 473-497.

Newman et al., "Synthesis of Two Chromoplast-Specific Proteins During Fruit Development in Capsicum Annuum", Plant Physiology, vol. 91, 1989, pp. 455-458.

Nikova et al., "Overcoming of Interspecies Incompatibility in the Solanaceaous Genera *Nicotiana* and *Capsicum* via In Vitro Techniques", In Vitro Cellular and Developmental Biology, Animal, vol. 37, No. 3, Part 2, Mar. 2001, p. 40-A.

NL PBR PPS1165. Sweet 46, Filed Oct. 23, 2009. Granted on Jan. 27, 2012, 7 pages.

Onus et al., "Monogenic Segregations in Backcross Progenies of Capsicum Baccatum x Two Interspecific $F_1$ Hybrids and Some Possible Explanations for Distorted Segregation Ratios in Capsicum", Turkish Journal of Botany, vol. 24, 2000, pp. 319-328.

Oren-Shamir et al., "Occurrence of the chromoplast protein ChrA correlates with a fruit-color gene in Capsicum annum", Plant Molecular Biology, vol. 21, 1993, pp. 549-554.

Osuna-Garcia et al., "Endogenous Levels of Tocopherols and Ascorbic Acid during Fruit Ripening of New Mexican~ Type Chile (*Capsicum annuum* L.) Cultivars", Journal of Agricultural and Food Chemistry, vol. 46, No. 12, 1998, pp. 5093-5096.

Park et al., "Susceptibilization of Red Pepper *Capsicum annuum* L. To Colletotrichum-Gloeosporioides Penz. in Relation to The Ripening of Fruits", Korean Journal of Plant Pathology, vol. 5, No. 3, 1989, pp. 262-270 (English Abstract Only).

"Pepper Capsicum Annum Marconi Red", Uploaded from davesgarden.com, 2013, 1 page.

Poehlman et al., "Methods in Plant Breeding", Breeding Field Crops, 4th edition, 1995, pp. 172-174.

Qin et al., "Whole-Genome Sequencing of Cultivated and Wild Peppers provides Insights into Capsicum Domestication and Specialization", PNAS, vol. 111, No. 14, Apr. 8, 2014, pp, 5135-5140.

Quiros, Carlos F., "Solanacea: PEPPER: *Capsicum* spp", VC 221, online fact sheet from www.plantsciences.ucdavis.edu/vc221/pepper, Apr. 2003, 3 pages.

Sahin et al., "Resistance in Capsicum Pubescens to *Xanthomonas campestris* Pv. Vesicatoria Pepper Race 6", Plant Disease, vol. 82 No. 7, Jul. 1998, pp. 794-799.

Shifriss et al., "Studies of the Inheritance of Mature Fruit Color in *Capsicum annuum* L.", Euphytica, vol. 60, 1992, pp. 123-126.

Sibi et al., "Obtention De Plantes Haploides Par and Rogenese in Vitro Chez Le Piment (*Capsicum* L.)", Ann. Amelior. Plantes, vol. 29, No. 5, 1979, pp. 583-606. (See Communication under 37 CFR § 1.98(a) (3)).

Simpson et al., "Chromoplast Ultrastructure of Capsicum Carotenoid Mutants II. Effect of Light and CPTA", Z. Pflanzenphysiol. Bd., vol. 83, 1977, pp. 309-325.

Smith, Paul G., "Inheritance of Brown and Green Mature Fruit Color in Peppers", Journal of Heredity, vol. 41, No. 5, 1950, pp. 138-140.

Syngenta Seeds B.V., "PVR 20111337 ('Waltz')", filed on May 23, 2011, Granted Dec. 17, 2012, pp. 1-4.

Thorup et al., "Candidate Gene Analysis of Organ Pigmentation Loci in the Solanaceae", PNAS, vol. 97, No. 21, Oct. 10, 2000, pp. 11192-11197.

Tong et al., "Capsicum Tovarii, A New Member of the Capsicum Baccatum Complex", Euphytica, vol. 109, 1999, pp. 71-77.

Van Der Heiden, Anton A, U.S. Appl. No. 12/961,222, filed Dec. 6, 2010, titled "Pepper Hybrid E490264".

Yoon et al., "Interspecific Cross Compatibility among Five Domesticated Species of *Capsicum* Genus", Journal of the Korean Society for Horticultural Science, vol. 45, No. 6, 2004, pp. 324-329.

Zijlstra et al., "Pollen Tube Growth in Interspecific Crosses between *Capsicum* Species", HortScience, vol. 26, No. 5, 1991, pp. 585-586.

Yeam et al., "Allele-specific CAPS Markers based on Point Mutations in Resistance Alleles at the pvr1 Locus Encoding elF4E in Capsicum", Theoretical and Applied Genetics, vol. 112, 2005, pp. 178-186.

\* cited by examiner

```
  1 TCTAGCAATAGAGAGCCTTTGAATTAATATGATAGTTTTGAAGCACTG TTTCATTTTAA  60
    ||||||||||||||||||||||||||||||||||||||||||||||||  |||||||||||
  1 TCTAGCAATAGAGAGCCTTTGAATTAATATGATAGTTTTGAAGCACTG TTTCATTTTAA  60

61 TTTCTTAGGTTATTTTCATCTTTT TCAATGCAAAAGTGAAACAAAAGCTATACACATTG 120
    |||||||||||||||||||||||| ||||||||||||||||||||||||||||||||||||
 61 TTTCTTAGGTTATTTTCATCTTTT TCAATGCAAAAGTGAAACAAAAGCTATACACATTG 120

121 TCATCGTTGTTCAAAC 136 (SEQ ID NO: 4)
    ||||||||||||||||
121 TCATCGTTGTTCAAAC 136 (SEQ ID NO: 5)
```

RED-YELLOW STRIPED PEPPERS

CROSS REFERENCE TO RELATED APPLICATIONS

This application is a Continuation-In-Part application of U.S. application Ser. No. 14/121,903, filed Oct. 30, 2014, which claims the benefit of U.S. Provisional Application Ser. No. 61/899,010, filed Nov. 1, 2013, and this application also claims the priority benefit of U.S. Provisional Application Ser. No. 62/326,619, filed Apr. 22, 2016, and U.S. Provisional Application Ser. No. 62/366,927, filed Jul. 26, 2016, each of which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 701802011300SEQLIST.txt, date recorded: Apr. 19, 2017, size: 10 KB).

FIELD OF THE INVENTION

The present disclosure relates to the field of plant breeding. In particular, the present disclosure relates to new and distinctive chimeric pepper plants (*Capsicum annuum*) that produce yellow and red striped pepper fruit.

BACKGROUND

The bell pepper (*Capsicum annuum*) originated in Mexico and the neighboring areas of Central America. Soon after Columbus's discovery of this plant, it was grown worldwide and used as a spice and a medicine. Today, pepper plants can be found growing wild in tropical areas around the world. Many countries grow it as a crop. Many of the hot peppers can be found in Latin America and China, but the United States prefers bell peppers. Peppers are used for fresh consumption, and they are processed into powders, sauces, and salsas. Many of the new cultivars grown today can be traced back to the early plants.

The genus *Capsicum* and species *annuum* includes most of the peppers grown in the United States. These can be further grouped into two broad categories: chili peppers which are pungent (hot) and sweet peppers which are non-pungent (mild). The United States produces four percent of the world's *Capsicum* peppers (sweet and hot), ranking sixth behind China, Mexico, Turkey, Spain and Nigeria. Bell peppers are the most common sweet pepper and are found in virtually every retail produce department. Grown commercially in most states, the U.S. industry is largely concentrated in California and Florida, which together accounted for 78% of output in 2000. New Jersey, Georgia, and North Carolina round out the top five producing states (Economic Research Service, USDA, Vegetables and Melons Outlook/VGS-288/Dec. 14, 2001).

Bell peppers are eaten raw, cooked, immature and mature. Often nutritional content is altered by the changes in the way they are consumed. Per capita consumption of bell peppers in 1995 was 6.2 pounds. They are an excellent source of Vitamin C, Vitamin A, and Calcium. Red peppers have more of these qualities than the immature green peppers.

Peppers grown in temperate regions are herbaceous annuals, but are herbaceous perennials where temperatures do not drop below freezing. Pepper plants' growth habit may be prostrate, compact, or erect, but it is determinate in that after it produces nine to eleven leaves a single stem terminates in flowers. These plants are grown for the edible fleshy fruit produced by this dichotomous growth. Peppers are non-climacteric which means they do not produce ethylene. They need to stay on the vine to continue the ripening process. A deep taproot will form if the plant root system is uninjured during transplanting. The spindle root will develop fibrous secondary root systems spreading laterally and downward. On the soil surface the stem will produce adventitious roots, but not as easily as tomatoes. The leaves of the pepper plant arise singly and are simple, entire, and asymmetrical. Typical of all Solanaceous plants, the leaves are arranged alternately on the stem. They are shiny and glabrous and vary in shape from broadly ovate to ovate lanceolate. The flowers develop singly or in twos or threes continuously as the upper structure of the plant proliferates. The corolla is white and five lobed while the anthers are bluish or yellowish in color. The flowers have an open anther formation and will indefinitely self-pollinate. They are also pollinated by insects, which increases the chances of cross-pollination. Unlike tomatoes, whose pollen becomes nonviable in high temperatures, the pepper flowers' pollen is not extremely heat sensitive and it remains viable up to 100° Fahrenheit producing fruit throughout the season.

Pepper is an important and valuable field crop. Thus, there is a continued need for new and interesting peppers.

BRIEF SUMMARY

In order to meet these needs, the present disclosure is directed to improved hybrid peppers. In certain aspects, the present disclosure relates to a pepper, *Capsicum annuum*, seed comprising a yellow allele and a red allele at the capsanthin-capsorubin synthase (CCS) locus, and produces a chimeric pepper plant comprising a first tissue, wherein the first tissue is an epidermal peel, septum, sepal, petal, anther, or leaf tissue comprising only a yellow allele at the CCS locus, and a second tissue comprising a red allele and a yellow allele at the CCS locus. In certain embodiments, the second tissue is one or more of filament, placenta, sepal, petal, ovary, anther, vascular, and stem tissue. In some embodiments, the seed produces a chimeric pepper plant that produces pepper fruit having a yellow and red striped color. In some embodiments, the red allele comprises a sequence having at least 90% identity to SEQ ID NO: 1. In some embodiments, the seed produces a chimeric pepper plant that produces chimeric pericarp tissue comprising one or more regions having a yellow color, comprising only a yellow allele at the CCS locus, and one or more regions having a red color, comprising a red allele at the CCS locus. In certain embodiments, the seed is produced from a cross between a first pepper plant that produces pepper fruit having a yellow color and second pepper plant that produces pepper fruit having a red color. In one embodiment, the first pepper plant is a pepper plant from the 'OP.1745' pepper plant variety, and the second pepper plant is a pepper plant that produces fruit having a red color. In one embodiment, the first pepper plant is a pepper plant from the 'OP.1745' pepper plant variety, and the second pepper plant is a pepper plant from the 'OP.2023' pepper plant variety. In another embodiment, the first pepper plant is a pepper plant from the 'OP.1745' pepper plant variety, and the second pepper plant is a pepper plant from the 'OP.1755' pepper plant variety. In yet another embodiment, the first pepper plant is a pepper plant from the 'OP.1745' pepper plant variety, and the second pepper plant is a pepper plant from the 'OP.0900' pepper plant variety.

Certain aspects of the present disclosure relate to *Capsicum annuum* chimeric pepper plants and plant parts isolated therefrom produced by growing any of the pepper seeds described herein. Chimeric pepper plants of the present disclosure produce pepper fruit having a yellow and red striped color. In certain embodiments, the present disclosure relates to *Capsicum annuum* chimeric pepper plants and plant parts isolated therefrom having all the physiological and morphological characteristics of a *Capsicum annuum* pepper plant produced by growing the pepper seeds described herein. Pepper plant parts include pepper leaves, ovules, pollen, seeds, pepper fruits, parts of pepper fruits, flowers, cells, and the like. In some embodiments, the present disclosure is directed to pepper leaves, ovules, pollen, seeds, pepper fruits, parts of pepper fruits, and/or flowers isolated from the chimeric pepper plants. In one embodiment, the plant part is a pepper fruit. In another embodiment, the present disclosure further relates to protoplasts produced from the chimeric pepper plants. In another embodiment, the present disclosure further relates to tissue culture of chimeric pepper plants produced from a plant part selected from leaf, anther, pistil, stem, petiole, root, root tip, fruit, seed, flower, cotyledon, hypocotyl, embryo and meristematic cell.

Certain aspects of the present disclosure relate to a method of generating and selecting a chimeric pepper plant that produces pepper fruit having a yellow and red striped color. In some embodiments, the method includes the steps of crossing a first pepper plant comprising two red alleles at the CCS locus with a second pepper plant comprising at least one yellow allele at the CCS locus to create $F_1$ hybrid progeny, growing the $F_1$ hybrid progeny to produce a population of $F_1$ hybrid progeny plants, and selecting from the population of $F_1$ hybrid progeny plants one or more $F_1$ hybrid progeny plants comprising one or more tissues with only the yellow allele at the CCS locus. In certain embodiments, the one or more selected $F_1$ hybrid progeny plants produce pepper fruit having yellow and red striped color. In certain embodiments, the first pepper plant produces red pepper fruit and the second pepper plant produces yellow pepper fruit. In certain embodiments, the first pepper plant is from an 'OP.2023' pepper plant variety, an 'OP.1755' pepper plant variety, or an 'OP.0900' pepper plant variety, and the second pepper plant is from an 'OP.1745' pepper plant variety. In certain embodiments, plant material of plants from the population of $F_1$ hybrid progeny plants is screened to identify plants containing one or more tissues with only the yellow allele at the CCS locus. In one embodiment, the plant material includes any combination of leaf material, epidermal peel material, and septum material. In one embodiment, the screening is accomplished by performing single nucleotide polymorphism (SNP) analysis of the plant material. In certain embodiments, $F_1$ hybrid progeny plants containing one or more tissues with only the yellow allele at the CCS locus are selected and propagated.

Certain aspects of the present disclosure relate to a method of vegetatively propagating a chimeric pepper plant that produces pepper fruit having a yellow and red striped color, wherein the method includes the steps of selecting plant material from a chimeric pepper plant that produces pepper fruit having a yellow and red striped color, and vegetatively propagating the selected plant material to asexually reproduce progeny pepper plants that also produce pepper fruit having a yellow and red striped color. In one embodiment, the plant material is sympodial shoot material. In another embodiment, the plant material is main branch material. In yet another embodiment, the plant material is from a branch that produces pepper fruit having a yellow and red striped color. In certain embodiments, the method increases the likelihood of producing progeny pepper plants that produce pepper fruit having yellow and red striped color. In one embodiment, the method produces 85% or more progeny pepper plants that produce pepper fruit having a yellow and red striped color. In other embodiments, the method reduces the likelihood of producing off-type progeny pepper plants that produce pepper fruit having only a single color. In one embodiment, the method produces 15% or fewer off-type progeny pepper plants that produce pepper fruit having only a single color.

Other aspects of the present disclosure relate to a method of vegetatively propagating a chimeric pepper plant that produces pepper fruit having a yellow and red striped color, wherein the method includes the steps of screening plant material from a chimeric pepper plant that produces pepper fruit having a yellow and red striped color, selecting plant material based upon the results of the screening, and vegetatively propagating the selected plant material to asexually reproduce progeny pepper plants that also produce pepper fruit having a yellow and red striped color. In some embodiments, the screening includes performing single nucleotide polymorphism (SNP) analysis on the plant material. In some embodiments, the plant material is an anther. In certain embodiments, the plant material is selected based upon the plant material being heterozygous for one or more portions of chromosome six. In one embodiment, the one or more portions of chromosome six is the portion spanning position 0.92 Mbp and 180 Mbp on chromosome six. In another embodiment, the one or more portions of chromosome six is the portion spanning position 0.92 Mbp and 22 Mbp on chromosome six. In yet another embodiment, the one or more portions of chromosome six is the portion containing the CCS locus. In certain embodiments, the plant material is selected based upon being heterozygous at the CCS locus. In certain embodiments, the method increases the likelihood of producing progeny pepper plants that produce pepper fruit having yellow and red striped color. In one embodiment, the method produces 85% or more progeny pepper plants that produce pepper fruit having a yellow and red striped color. In other embodiments, the method reduces the likelihood of producing off-type progeny pepper plants that produce pepper fruit having only a single color. In one embodiment, the method produces 15% or fewer off-type progeny pepper plants that produce pepper fruit having only a single color.

Other aspects of the present disclosure relate to chimeric pepper plants produced by any of the methods described herein.

In addition to the exemplary aspects and embodiments described above, further aspects and embodiments will become apparent by reference by study of the following descriptions.

BRIEF DESCRIPTION OF THE DRAWINGS

The patent or application file contains at least one drawing executed in color. Copies of this patent or patent application publication with color drawings will be provided by the office upon request and payment of the necessary fee.

FIG. 3 shows the marker profiles for markers located on chromosomes five, six, and seven of the 'OP.1745', 'OP.2023', 'Maduro', and RY1 plants. The marker base pair positions are based on the Zunla reference genome.

FIG. 4 shows a sequence alignment of the portion of the capsanthin-capsorubin synthase genomic locus for the red (SEQ ID NO: 4) and yellow (SEQ ID NO: 5) alleles used for the CAM000413 marker analysis. Underlined sequences represent sites for the forward and reverse primers used for PCR amplification of these sequences, and highlighted nucleotides indicate SNPs detected between the red and yellow alleles.

FIG. 7A shows a side/bottom view of a yellow and red striped fruit of a chimeric pepper plant (RY5). FIG. 7B shows a side view of two yellow and red striped fruit of a chimeric pepper plant (RY5), as well as an unripened fruit. FIG. 7C shows a side view of two yellow and red striped fruit of a chimeric pepper plant (RY5), as well as two unripened fruit. FIG. 7D shows a side view of two yellow and red striped fruit of a chimeric pepper plant (RY5), as well as two unripened fruit.

DETAILED DESCRIPTION

Figure 1:
FIG. 1 shows top and side views of several yellow and red striped fruit (RY1).

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The selected germplasm is crossed in order to recombine the desired traits and through selection varieties or parent lines are developed. The goal is to combine in a single variety or hybrid an improved combination of desirable traits from the parental germplasm. These important traits may include higher yield, field performance, fruit and agronomic quality such as fruit shape and length, resistance to diseases and insects, and tolerance to drought and heat.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s) for three years at least. The best lines are candidates for new commercial cultivars; those still deficient in a few traits are used as parents to produce new populations for further selection. These processes, which lead to the final step of marketing and distribution, usually take from five to ten years from the time the first cross or selection is made.

One goal of pepper plant breeding is to develop new, unique and superior pepper cultivars. A breeder can initially select and cross two or more parental lines, followed by repeated selfing and selection, producing many new genetic combinations. Moreover, a breeder can generate multiple different genetic combinations by crossing, selfing, and mutations. A plant breeder can then select which germplasms to advance to the next generation. These germplasms may then be grown under different geographical, climatic, and soil conditions, and further selections can be made during, and at the end of, the growing season.

The development of commercial pepper cultivars thus requires the development of pepper parental lines, the crossing of these lines, and the evaluation of the crosses. Pedigree breeding and recurrent selection breeding methods are used to develop cultivars from breeding populations. Breeding programs combine desirable traits from two or more varieties or various broad-based sources into breeding pools from which lines are developed by selfing and selection of desired phenotypes. The new lines are crossed with other lines and the hybrids from these crosses are evaluated to determine which have commercial potential.

Pedigree breeding is used commonly for the improvement of self-pollinating crops or inbred lines of cross-pollinating crops. Two parents which possess favorable, complementary traits are crossed to produce an $F_1$. An $F_2$ population is produced by selfing one or several $F_1$s or by intercrossing two $F_1$s (sib mating). Selection of the best individuals is usually begun in the $F_2$ population; then, beginning in the $F_3$, the best individuals in the best families are selected. Replicated testing of families, or hybrid combinations involving individuals of these families, often follows in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding may be used to transfer genes for a simply inherited, highly heritable trait into a desirable homozygous cultivar or line that is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In addition to phenotypic observations, the genotype of a plant can also be examined. There are many laboratory-based techniques available for the analysis, comparison and characterization of plant genotype; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length polymorphisms (AFLPs), Simple Sequence Repeats (SSRs—which are also referred to as Microsatellites), and Single Nucleotide Polymorphisms (SNPs).

Molecular markers, or "markers", can also be used during the breeding process for the selection of qualitative traits. For example, markers closely linked to alleles or markers containing sequences within the actual alleles of interest can be used to select plants that contain the alleles of interest. The use of markers in the selection process is often called genetic marker enhanced selection or marker-assisted selection. Methods of performing marker analysis are generally known to those of skill in the art.

Mutation breeding may also be used introducing new traits into pepper varieties. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation (such as X-rays, Gamma rays, neutrons, Beta radiation, or ultraviolet radiation), chemical mutagens (such as base analogs like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid or acridines. Once a desired trait is observed through mutagenesis the trait may then be incorporated into existing germplasm by traditional breeding techniques. Details of mutation breeding can be found in *Principles of Cultivar Development* by Fehr, Macmillan Publishing Company, 1993.

The production of double haploids can also be used for the development of homozygous lines in a breeding program. Double haploids are produced by the doubling of a set of chromosomes from a heterozygous plant to produce a completely homozygous individual. For example, see Wan, et al., *Theor. Appl. Genet.*, 77:889-892, 1989.

Additional non-limiting examples of breeding methods that may be used include, without limitation, those found in *Principles of Plant Breeding*, John Wiley and Son, pp. 115-161, 1960; Allard, 1960; Simmonds, 1979; Sneep et al., 1979; Fehr, 1987; "Carrots and Related Vegetable Umbelliferae", Rubatzky, V. E., et al., 1999.

Definitions

In the description and tables that follow, a number of terms are used. In order to provide a clear and consistent understanding of the specification and claims, including the scope to be given such terms, the following definitions are provided:

As used herein, the term "allele" refers to any of one or more alternative forms of a gene, all of which relate to one trait or characteristic. In a diploid cell or organism, the two alleles of a given gene occupy corresponding loci on a pair of homologous chromosomes.

As used herein, the term "zygosity" refers to the degree of similarity of the alleles for a trait. For diploid organisms, a locus may be homozygous (the two alleles are the same), heterozygous (the two alleles are different), and hemizygous (one allele is missing).

As used herein, the term "backcrossing" refers to a process in which a breeder repeatedly crosses hybrid progeny back to one of the parents, for example, a first generation hybrid $F_1$ with one of the parental genotype of the $F_1$ hybrid.

As used herein, the term "covered cultivation" refers to any type of cultivation where the plants are not exposed to direct sunlight. The covering includes, but is not limited to, greenhouses, glasshouses, net-houses, plastic houses, and tunnels.

As used herein, the term "essentially all the physiological and morphological characteristics" refers to a plant having the physiological and morphological characteristics of the recurrent parent.

As used herein, the term "pepper fruit" refers to a fruit produced by a *Capsicum annuum* plant, commonly referred to as a bell pepper. The color of a pepper fruit can be green, red, yellow, orange and, more rarely, white, black, and brown, depending on when they are harvested and the specific cultivar. Green peppers are unripe bell peppers, while the others are all ripe, with the color variation based on cultivar selection.

As used herein, the term "propagate" refers to reproducing a plant by means including, but not limited to, seeds, cuttings, divisions, tissue culture, embryo culture or other in vitro method.

As used herein, the term "regeneration" refers to the development of a plant from tissue culture.

Chimeric Pepper Seeds and Plants

Certain aspects of the present disclosure relate to chimeric pepper plants that produce pepper fruit having a yellow and red striped, patched, and/or variegated color, and to seeds that produce the chimeric pepper plants described herein.

Seeds

Certain aspects of the present disclosure relate to one or more seeds that produce chimeric pepper plants described herein. In some embodiments, the seed comprises a yellow allele and a red allele at the capsanthin-capsorubin synthase (CCS) locus.

In some embodiments, the seed produces a chimeric pepper plant comprising a first tissue comprising only a yellow allele at the CCS locus and a second tissue comprising a red allele and a yellow allele at the CCS locus. In some embodiments, the first tissue is one or more of e epidermal peel, septum, sepal, petal, anther, or leaf tissue. In some embodiments, the second tissue is one or more of filament, placenta, sepal, petal, anther, ovary, vascular, and stem tissue. In some embodiments, the seed produces a chimeric pepper plant that produces chimeric pericarp having one or more regions having a yellow color and comprising only a yellow allele at the CCS locus. In some embodiments, the seed produces a chimeric pepper plant that produces chimeric pericarp having one or more regions having a red color and comprising a red allele at the CCS locus. In some embodiments, the seed produces a chimeric pepper plant that produces chimeric pericarp having one or more regions having a yellow color and comprising only a yellow allele at the CCS locus and one or more regions having a red color and comprising a red allele at the CCS locus. In some embodiments, the seed produces a chimeric pepper plant that produces pepper fruit having a yellow and red striped, patched, and/or variegated color.

In some embodiments, the seed is produced from a cross between a first pepper plant and a second pepper plant. In some embodiments, the first pepper plant is a pepper plant comprising a yellow allele at the CCS locus. In some embodiments, the first pepper plant is a pepper plant that produces pepper fruit having a yellow color. In some embodiments, the second pepper plant is a pepper plant comprising a red allele at the CCS locus. In some embodiments, the second pepper plant is a pepper plant that produces pepper fruit having a red color. In some embodiments, the first pepper plant is an 'OP.1745' pepper plant variety. In some embodiments, the second pepper plant is an 'OP.2023' pepper plant variety, an 'OP.1755' pepper plant variety, or an 'OP.0900' pepper plant variety.

In some embodiments, the seed is produced from a cross between an 'OP.1745' pepper plant variety and a second pepper plant variety. In some embodiments, the second pepper plant is a pepper plant comprising a red allele at the CCS locus. In some embodiments, the second pepper plant variety is a pepper plant that produces pepper fruit having a red color. In some embodiments, the second pepper plant variety is an 'OP.2023' pepper plant variety, an 'OP.1755' pepper plant variety, or an 'OP.0900' pepper plant variety.

In some embodiments, the seed is produced from a cross between an 'OP.1745' pepper plant variety and an 'OP.2023' pepper plant variety. In some embodiments, the seed is produced from a cross between an 'OP.1745' pepper plant variety and an 'OP.1755' pepper plant variety. In some embodiments, the seed is produced from a cross between an 'OP.1745' pepper plant variety and an 'OP.0900' pepper plant variety.

Chimeric Pepper Plants

Certain aspects of the present disclosure relate to chimeric pepper plants that produce pepper fruit having a yellow and red striped, patched, and/or variegated color. In some embodiments, the chimeric pepper plants are produced from the pepper seeds described herein.

In some embodiments, the chimeric pepper plant comprises a first tissue comprising only a yellow allele at the CCS locus and a second tissue comprising a red allele and a yellow allele at the CCS locus. In some embodiments, the first tissue comprising only a yellow allele at the CCS locus is one or more of epidermal peel, septum, sepal, petal, anther, and leaf tissue. In some embodiments, the first tissue is epidermal peel tissue. In some embodiments, the first tissue is septum tissue. In some embodiments, the first tissue is sepal tissue. In some embodiments, the first tissue is petal tissue. In some embodiments, the first tissue is anther tissue. In some embodiments, the first tissue is leaf tissue. In some embodiments, the second tissue comprising a red allele and a yellow allele at the CCS locus is one or more of filament, placenta, sepal, petal, ovary, anther, vascular, and stem tissue. In some embodiments, the second tissue is filament tissue. In some embodiments, the second tissue is placenta tissue. In some embodiments, the second tissue is sepal tissue. In some embodiments, the second tissue is petal tissue. In some embodiments, the second tissue is ovary tissue. In some embodiments, the second tissue is anther tissue. In some embodiments, the second tissue is vascular tissue. In some embodiments, the second tissue is stem tissue.

In some embodiment, the chimeric pepper plant produces chimeric pericarp tissue. In some embodiments, the chimeric pericarp tissue comprises one or more (e.g., at least one, at least two, at least three, at least four, at least five or more) regions having a yellow color. In some embodiments, the chimeric pericarp tissue comprises one or more (e.g., at least one, at least two, at least three, at least four, at least five or more) regions comprising only a yellow allele at the CCS locus. In some embodiments, the chimeric pericarp tissue comprises one or more (e.g., at least one, at least two, at least three, at least four, at least five or more) regions having a yellow color and comprising only a yellow allele at the CCS locus. In some embodiments, the chimeric pericarp tissue comprises one or more (e.g., at least one, at least two, at least three, at least four, at least five or more) regions having a red color. In some embodiments, the chimeric pericarp tissue comprises one or more (e.g., at least one, at least two, at least three, at least four, at least five or more) regions comprising a red allele at the CCS locus. In some embodiments, the chimeric pericarp tissue comprises one or more (e.g., at least one, at least two, at least three, at least four, at least five or more) regions having a red color and comprising a red allele at the CCS locus. In some embodiments, the chimeric pericarp tissue comprises one or more (e.g., at least one, at least two, at least three, at least four, at least five or more) regions having a yellow color and one or more (e.g., at least one, at least two, at least three, at least four, at least five or more) regions having a red color. In some embodiments, the chimeric pericarp tissue comprises one or more (e.g., at least one, at least two, at least three, at least four, at least five or more) regions comprising only a yellow allele at the CCS locus and one or more (e.g., at least one, at least two, at least three, at least four, at least five or more) regions comprising a red allele at the CCS locus. In some embodiments, the chimeric pericarp tissue comprises one or more regions having a yellow color and comprising only a yellow allele at the CCS locus and one or more regions having a red color and comprising a red allele at the CCS locus. In some embodiments, the chimeric pericarp tissue appears striped, with alternating red and yellow colors. In some embodiments, the chimeric pericarp tissue appears patched, with alternating red and yellow colors. In some embodiments, the chimeric pericarp tissue appears variegated, with alternating red and yellow colors.

In some embodiments, a chimeric pepper plant of the present disclosure produces pepper fruit having a yellow and red striped, patched, or variegated color. In some embodiments, a chimeric pepper plant of the present disclosure produces pepper fruit having a yellow and red striped color. In some embodiments, a chimeric pepper plant of the present disclosure produces pepper fruit having a yellow and red patched color. In some embodiments, a chimeric pepper plant of the present disclosure produces pepper fruit having a yellow and red variegated color. In some embodiments, the chimeric pepper plant produces pepper fruit that appears striped, with alternating yellow and red colors. In some embodiments, the chimeric pepper plant produces pepper fruit that appears patched, with alternating yellow and red colors. In some embodiments, the chimeric pepper plant produces pepper fruit that appears variegated, with alternating yellow and red colors.

In some embodiments, the present disclosure relates to one or more plant parts from any of the chimeric pepper plants described herein. In some embodiments, the plant part is a leaf, a seed, a fruit, a cell, or any portion thereof. In some embodiments, the plant part is a fruit. In some embodiments, the fruit is a pepper fruit having yellow and red striped, patched, and/or variegated colors.

In some embodiments, the present disclosure relates to one or more pollen grains or one or more ovules from any of the chimeric pepper plants described herein. In some embodiments, the present disclosure relates to a pollen grain from any of the chimeric pepper plants described herein. In some embodiments, the present disclosure relates to an ovule from any of the chimeric pepper plants described herein.

In some embodiments, the present disclosure relates to one or more protoplasts produced from any of the chimeric pepper plants described herein.

In some embodiments, the present disclosure relates to tissue culture produced from protoplasts or cells from any of the chimeric plant pepper plants described herein. In some embodiments, the protoplasts and/or cells are produced from one or more plant parts from any of the chimeric plant pepper plants described herein. In some embodiments, the plant part is one or more of leaf, anther, pistil, stem, petiole, root, root tip, fruit, seed, flower, cotyledon, hypocotyl, embryo, and meristematic cells.

Without wishing to be bound by theory, the chimeric pepper plants of the present disclosure may be produced from seed comprising both a yellow allele and a red allele from the parental pepper plants, but some of the tissues in the chimeric pepper plant have lost the parental red allele, while other tissues of the chimeric pepper plant have retained the parental red allele. In some embodiments, the embryo may have formed with heterogeneous sections of cells, some of which contain only the parental red allele, and some of which contain only the parental yellow allele. These heterogeneous sections of cells may be characterized as periclinal, mericlinal, or sectorial. In some embodiments, heterogeneous sections of cells may have formed within the meristems of the adult plant, and these sections may be characterized as periclinal, mericlinal, or sectorial. In some embodiments, a mutation in a plastid gene or altered plastid gene expression may cause the chimeric phenotype. In some embodiments, altered plastid inheritance patterns may cause the phenotype. In some embodiments, carotenoid synthetic pathways or carotenoid accumulation may be affected by plastid alterations, nuclear genome alterations, or developmental perturbations. In some embodiments, the nuclear genome of the hybrid may be incompatible with one parental plastid. In some embodiments, alleles from the maternal and paternal genomes may interact disharmoniously within the hybrid. In some embodiments, a mutation may be present that inhibits correct mitosis or meiosis. In some embodiments, a mutation may be present that inhibits correct nuclear fusion during fertilization, giving rise to a genetically mosaic embryo. In some embodiments, a transacting factor such as a transposon may have removed an allele, a region containing an allele, or a segment of an allele. In some embodiments, a transacting factor such as a transposon may have integrated into an allele, and caused the allele to become non-functional. In some embodiments, a portion of the chromosome comprising the red and/or yellow alleles may be more susceptible to DNA damage than other areas of the pepper genome. In some embodiments, some tissues from the chimeric pepper plant may have lost the red allele due to homologous recombination, wherein a portion of the chromosome carrying the yellow allele from one parental pepper plant replaces the portion of the chromosome carrying the red allele from the other parental pepper plant. In some embodiments, the tissues having lost the red allele due to homologous recombination would be homozygous for at least a portion of the parental chromosome carrying the yellow allele. In some embodiments, some tissues from the chimeric pepper plant may have lost at least a portion of the chromosomes comprising the red allele due to genomic instability. In some embodiments, loss of at least a portion of the chromosome carrying the red allele may lead to tissues that are hemizygous for at least a portion of the parental chromosome carrying the yellow allele. In some embodiments, the genomic instability may be due to genomic instability on the chromosome comprising the red or yellow alleles. In some embodiments, the genomic instability may be on a chromosome that does not comprise the red or yellow alleles, but induces loss of at least a portion of the chromosome carrying the red allele. In some embodiments, the genomic instability may be due to a transacting factor, such as a transposon, causing instability on the chromosome carrying the red or yellow alleles. In some embodiments, the genomic instability may be due to invasion by a foreign element, such as a virus.

Red and Yellow CCS Alleles

In some embodiments, a pepper seed, tissue, organ, plant part, and/or plant comprising a red allele at the CCS locus is a pepper seed, tissue, organ, plant part, and/or plant with a genomic locus comprising a polynucleotide of SEQ ID NO: 1. In some embodiments, a pepper seed, tissue, organ, plant part, and/or plant comprising a red allele at the CCS locus is a pepper seed, tissue, organ, plant part, and/or plant with a genomic locus comprising a polynucleotide having at least 90%, at least 91%, at least 92%, at least 93%, at least 94%, at least 95%, at least 96%, at least 97%, at least 98%, at least 99%, or 100% identity to the sequence of SEQ ID NO: 1.

In some embodiments, a pepper seed, tissue, organ, plant part, and/or plant comprising a red allele at the CCS locus is a pepper seed, tissue, organ, plant part, and/or plant which encodes a polynucleotide of SEQ ID NO: 2. In some embodiments, a pepper seed, tissue, organ, plant part, and/or plant comprising a red allele at the CCS locus is a pepper seed, tissue, organ, plant part, and/or plant which encodes a polynucleotide having at least at least 90%, at least 91%, at least 92%, at least 93%, at least 94%, at least 95%, at least 96%, at least 97%, at least 98%, at least 99%, or 100% identity to the sequence of SEQ ID NO: 2.

In some embodiments, a pepper seed, tissue, organ, plant part, and/or plant comprising a red allele at the CCS locus is a pepper seed, tissue, organ, plant part, and/or plant comprising a polypeptide of SEQ ID NO: 3. In some embodiments, a pepper seed, tissue, organ, plant part, and/or plant comprising a red allele at the CCS locus is a pepper seed, tissue, organ, plant part, and/or plant comprising a polypeptide having at least 90%, at least 91%, at least 92%, at least 93%, at least 94%, at least 95%, at least 96%, at least 97%, at least 98%, at least 99%, or 100% identity to the sequence of SEQ ID NO: 3.

In some embodiments, a pepper seed, tissue, organ, plant part, and/or plant comprising a yellow allele at the CCS locus is a pepper seed, tissue, organ, plant part, and/or plant that produces a less functional or non-functional CCS gene product. In some embodiments, a pepper seed, tissue, organ, plant part, and/or plant that produces a less functional or non-functional CCS gene product is a pepper seed, tissue, organ, plant part, and/or plant comprising an inactivating mutation in the CCS gene. Examples of inactivating mutations may include, but are not limited to, point mutations, nonsense mutations, truncation mutations, missense mutations, substitution mutations, frameshift mutations, loss-of-function mutations, deletion mutations, insertion mutations, duplication mutations, amplification mutations, translocation mutations, or inversion mutations that result in a non-functional gene product encoded by the gene. In some embodiments, a pepper seed, tissue, organ, plant part, and/or plant that produces a less functional or non-functional CCS gene product is a pepper seed, tissue, organ, plant part, and/or plant comprising epigenetic modification to the CCS gene locus. In some embodiments, epigenetic modification to the CCS locus reduces or inhibits expression of the CCS gene product. In some embodiments, a pepper seed, tissue, organ, plant part, and/or plant that produces a less functional or non-functional CCS gene product is a pepper seed, tissue, organ, plant part, and/or plant comprising CCS gene product that has been inactivated. Examples of inactivated gene products may include, but are not limited to, gene products that are misfolded, gene products that are inhibited by post-translational modifications, gene products inhibited by binding to inhibitors, gene products that are chemically inhibited, and gene products that are mislocalized.

Methods of Generating and Selecting Chimeric Pepper Plants

Certain aspects of the present disclosure relate to methods of generating and selecting chimeric pepper plants that produce pepper fruit having a yellow and red striped, patched, and/or variegated color.

In some embodiments, the method of generating and selecting pepper plants that produce pepper fruit having a yellow and red striped, patched, and/or variegated color comprises crossing a first parental pepper plant and a second parental pepper plant. In some embodiments, the first parental pepper plant is the male parental pepper plant and the second parental pepper plant is the female parental pepper plant. In some embodiments, the first parental pepper plant is the female parental pepper plant and the second parental pepper plant is the male parental pepper plant. In some embodiments, the first parental pepper plant and the second pepper plant are plants from inbred pepper plant lines.

In some embodiments, the first parental pepper plant comprises at least one (e.g., one, two, or more) red alleles (R) at the CCS locus. In some embodiments, the first parental pepper plant comprises two red alleles (RR) at the CCS locus. In some embodiments, the first parental pepper plant comprises an (RR) genotype. In some embodiments, the first parental pepper plant comprises one red allele (R) and one yellow allele (r) at the CCS locus. In some embodiments, the first parental pepper plant comprises two red alleles (Rr) genotype. In some embodiments, the second parental pepper plant comprises at least one (e.g., one, two, or more) yellow alleles (r) at the CCS locus. In some embodiments, the second parental pepper plant comprises two yellow alleles (rr) at the CCS locus. In some embodiments, the second parental pepper plant comprises an (rr) genotype. In some embodiments, the second parental pepper plant comprises one yellow allele (r) and one red allele (R) at the CCS locus. In some embodiments, the second parental pepper plant comprises an (Rr) genotype.

In some embodiments, the method of generating chimeric pepper plants comprises crossing a first parental pepper plant comprising an (RR) or (Rr) genotype with a second parental pepper plant comprising an (Rr) or (rr) genotype to produce hybrid seed. In some embodiments, the first parental pepper plant comprises an (RR) genotype and the second parental pepper plant comprises an (Rr) genotype. In some embodiments, the first parental pepper plant comprises an (RR) genotype and the second parental pepper plant comprises an (rr) genotype. In some embodiments, the first parental pepper plant comprises an (Rr) genotype and the second parental pepper plant comprises an (Rr) genotype. In some embodiments, the first parental pepper plant comprises an (Rr) genotype and the second parental pepper plant comprises an (rr) genotype.

In some embodiments, the first parental pepper plant is an 'OP.2023' pepper plant variety, an 'OP.1755' pepper plant variety, or an 'OP.0900' pepper plant variety. In some embodiments, the first parental pepper plant is an 'OP.2023' pepper plant variety. In some embodiments, the first parental pepper plant is an 'OP.1755' pepper plant variety. In some embodiments, the first parental pepper plant is an 'OP.0900' pepper plant variety. In some embodiments, the second parental pepper plant is an 'OP.1745' pepper plant variety. In some embodiments, the cross between the first parental pepper plant and the second parental pepper plant comprises a cross between an 'OP.2023' pepper plant variety and an 'OP.1745' pepper plant variety. In some embodiments, the cross between the first parental pepper plant and the second parental pepper plant comprises a cross between an 'OP.1755' pepper plant variety and an 'OP.1745' pepper plant variety. In some embodiments, the cross between the first parental pepper plant and the second parental pepper plant comprises a cross between an 'OP.0900' pepper plant variety and an 'OP.1745' pepper plant variety.

In some embodiments, a cross between the first parental pepper plant and second parental pepper plant generates $F_1$ hybrid progeny. In some embodiments, the $F_1$ hybrid progeny is grown to create a population of $F_1$ hybrid progeny plants. In some embodiments, one or more $F_1$ hybrid progeny plants that produce pepper fruit having a yellow and red striped color are selected from the population of $F_1$ hybrid progeny plants. In some embodiments, the one or more selected $F_1$ hybrid progeny plants comprise one or more tissues comprising only a yellow allele at the CCS locus. In some embodiments, plant material from the population of $F_1$ hybrid progeny plants is screened to identify $F_1$ hybrid progeny plants comprising one or more tissues comprising only a yellow allele at the CCS locus. In some embodiments, the plant material is one or more of leaf, epidermal peel, and septum material. In some embodiments, the plant material is leaf material. In some embodiments, the plant material is epidermal peel material. In some embodiments, the plant material is septum material.

In some embodiments, screening plant material comprises performing marker analysis on the plant material. In some embodiments, the marker analysis is single nucleotide polymorphism (SNP) analysis. In some embodiments, the marker analysis indicates the zygosity of one or more chromosomes in the plant material. In some embodiments, the marker analysis indicates the zygosity of chromosome six in the plant material. Examples of markers on chromosome six may include, but are not limited to, CONTIG14444:607, CONTIG3495:1013, CONTIG13973:146, CONTIG15080:278, CAM0000501, CONTIG200085:278, CONTIG1349:1399, CONTIG5713:302, CONTIG1355:1037, CONTIG11146:187, CONTIGCAM0002444, CON- TIG8615:1817, CONTIG22248:401, CONTIG3916:1756, CONTIG7457:106, CAM0003794, CONTIG3740:1525, CONTIG462:888, CONTIG2594:540, CAM000413, and the markers described in Lefebvre, V. et al. Plant Mol Biol 1998 36(5) 785-789. In some embodiments, the marker is CAM000413. In some embodiments, the marker analysis indicates the zygosity of one or more portions of chromosome six in the plant material. In some embodiments, the one or more portions of chromosome six is the region spanning positions 0.92 Mbp and 180 Mbp on chromosome six. In some embodiments, the one or more portions of chromosome six is the region spanning positions 0.92 Mbp and 22 Mbp on chromosome six. In some embodiments, the positions on chromosome six are in relation to the corresponding positions on chromosome six in a reference genome. In some embodiments, the reference genome is the Zunla reference genome (Qin, C et al. Proc Natl Acad Sci USA. 2014 Apr. 8; 111(14):5135-40). In some embodiments, the one or more portions of chromosome six is the CCS locus. In some embodiments, the $F_1$ hybrid progeny plants comprising one or more tissues comprising only a yellow allele at the CCS locus are selected.

Methods of Reducing Propagation of Off-Type Pepper Plants

Certain aspects of the present disclosure relate to methods of vegetatively propagating any of the chimeric pepper plants described herein to produce progeny pepper plants that produce pepper fruit having a yellow and red striped, patched, and/or variegated color. In some embodiments, the method increases the likelihood of producing progeny pepper plants that produce pepper fruit having a yellow and red striped, patched, and/or variegated color. In some embodiments, the method reduces the likelihood of producing off-type progeny pepper plants that do not produce pepper fruit having a yellow and red striped, patched, and/or variegated color.

In some embodiments, the method comprises selecting plant material from the chimeric pepper plant, and vegetatively propagating the plant material. In some embodiments, the selected plant material is main branch material, sympodial shoot material, or material from a branch that already produces pepper fruit having yellow and red striped, patched, and/or variegated color. In some embodiments, the plant material is main branch material. In some embodiments the plant material is sympodial shoot material. In some embodiments, the plant material is from a branch that already produces pepper fruit having yellow and red striped, patched and/or variegated color. In some embodiments, the plant material is not axillary shoot material. In some embodiments, the plant material is not from a branch that produces pepper fruit having a single color.

In some embodiments, the method comprises screening plant material from the chimeric pepper plant, selecting plant material based upon the results of the screening, and vegetatively propagating the selected plant material. In some embodiments, screening plant material comprises performing marker analysis on the plant material. In some embodiments, the plant material is one or more of filament, placenta, sepal, petal, ovary, anther, vascular, and stem tissue. In some embodiments, the plant material is anther tissue. In some embodiments, the marker analysis is single nucleotide polymorphism (SNP) analysis. In some embodiments, the marker analysis indicates the zygosity of one or more chromosomes in the plant material. In some embodiments, the marker analysis indicates the zygosity of chromosome six in the plant material. Examples of markers on chromosome six may include, but are not limited to, CONTIG14444:607, CONTIG3495:1013, CONTIG13973:146, CONTIG15080:278, CAM0000501, CONTIG200085:278, CONTIG1349:1399, CONTIG5713:302, CONTIG1355:1037, CONTIG11146:187, CONTIGCAM0002444, CONTIG8615:1817, CONTIG22248:401, CONTIG3916:1756, CONTIG7457:106, CAM0003794, CONTIG3740:1525, CONTIG462:888, CONTIG2594:540, CAM000413, and the markers described in Lefebvre, V. et al. Plant Mol Biol 1998 36(5) 785-789. In some embodiments, the marker is CAM000413. In some embodiments, the marker analysis indicates the zygosity of one or more portions of chromosome six in the plant material. In some embodiments, the plant material is selected based upon the plant material being heterozygous for one or more portions of chromosome six. In some embodiments, the plant material is selected upon the plant material being heterozygous for the region spanning positions 0.92 Mbp and 180 Mbp on chromosome six. In some embodiments, the plant material is selected based upon the plant material being heterozygous for the region spanning positions 0.92 Mbp and 22 Mbp on chromosome six. In some embodiments, the positions on chromosome six are in relation to the corresponding positions on chromosome six in a reference genome. In some embodiments, the reference genome is the Zunla reference genome (Qin, C et al. Proc Natl Acad Sci USA. 2014 Apr. 8; 111(14):5135-40). In some embodiments, the plant material is selected based upon the plant material being heterozygous at the CCS locus.

In some embodiments, the method increases the likelihood of producing progeny pepper plants that produce pepper fruit having a yellow and red striped, patched, and/or variegated color. In some embodiments, the method produces 80%, 81%, 82%, 83%, 84%, 85%, 86%, 87%, 88%, 89%, 90%, 91%, 92%, 93%, 94%, 95%, 96%, 97%, 98%, 99%, or 100% progeny pepper plants that produce pepper fruit having a yellow and red striped, patched, and/or variegated color. In some embodiments, the method produces 80% or more progeny pepper plants that produce pepper fruit having a yellow and red striped, patched, and/or variegated color. In some embodiments, the method produces 85% or more progeny pepper plants that produce pepper fruit having a yellow and red striped, patched, and/or variegated color. In some embodiments, the method produces 90% or more progeny pepper plants that produce pepper fruit having a yellow and red striped, patched, and/or variegated color. In some embodiments, the method produces 95% or more progeny pepper plants that produce pepper fruit having a yellow and red striped, patched, and/or variegated color.

In some embodiments, the method reduces the likelihood of producing off-type progeny pepper plants that do not produce pepper fruit having a yellow and red striped, patched, and/or variegated color. In some embodiments, the method reduces the likelihood of producing off-type progeny pepper plants that produce pepper fruit having only a single color. In some embodiments, the off-type progeny pepper plants produce pepper fruit having a uniformly yellow color. In some embodiments, the method produces 20%, 19%, 18%, 17%, 16%, 15%, 14%, 13%, 12%, 11%, 10%, 9%, 8%, 7%, 6%, 5%, 4%, 3%, 2%, 1%, or 0% off-type progeny pepper plants. In some embodiments, the method produces 20% or fewer off-type progeny pepper plants. In some embodiments, the method produces 15% or fewer off-type progeny pepper plants. In some embodiments, the method produces 10% or fewer off-type progeny pepper plants. In some embodiments, the method produces 5% or fewer off-type progeny pepper plants.

Healey Mutant—RY5

'RY5' was discovered as a spontaneous mutant in a screening trial of mutants of pepper variety 'Healey' (not patented), conducted in Ontario, Canada in 2016 and in Michigan, United States in 2017. The mutant 'RY5' was selected based on its vertical red and yellow stripes color and propagated vegetatively (i.e., asexually).

The pepper plant variety 'RY5' has been asexually reproduced by cuttings at a farm in Ontario, Canada. Pepper plant variety 'RY5' is distinguished from all existing pepper plant varieties by the red and yellow striped fruit of the variety. The distinctive characteristics of pepper plant variety 'RY5' have been found to be stable and are transmitted to new pepper plants when asexually propagated.

The following botanical description is from fruit grown from plants vegetatively propagated from the original mutant 'RY5' pepper plant. Color references are primarily to the RHS Colour Chart of The Royal Horticultural Society of London (RHS) (2007 edition). Descriptive terminology follows the *Plant Identification Terminology, An Illustrated Glossary*, $2^{nd}$ edition by James G. Harris and Melinda Woolf Harris, unless where otherwise defined.

Hybrid pepper plant variety 'RY5' has the following morphologic and other characteristics:

| General: | |
|---|---|
| Usage: | Fresh market |
| Type of culture: | Covered cultivation (e.g., in greenhouse) |
| Plant: | |
| Seedling (anthocyanin coloration of hypocotyl): | Present |
| Stem length: | Medium |
| Shortened internode: | Absent |
| Internode length: | Medium to long |
| Anthocyanin coloration of nodes: | Present |
| Intensity of anthocyanin coloration of nodes on stem: | Medium to strong |
| Hariness of nodes on stem: | Medium |
| Plant height: | Medium to tall |
| Leaf shape: | Ovate |
| Undulation of leaf margin: | Weak |
| Leaf blistering: | Medium to strong |
| Leaf profile in cross section: | Moderately convex |
| Leaf glossiness: | Medium to strong |
| Peduncle attitude: | Semi-dropping |
| Leaf length of blade: | Medium to long |
| Leaf width of blade: | Medium to broad |
| Intensity of green color of leaf blade: | Medium to dark |
| Anthocyanin coloration in anther of flower: | Present |
| Time of beginning of flowering: | Medium |
| Time of maturity: | Medium |
| Fruit: | Images of the 'RY5' pepper fruit are presented in FIGS. 7A-7D. |
| Color before maturity: | Green |
| Intensity of color before maturity: | Medium |
| Anthocyanin coloration before maturity: | Absent |
| Attidue: | Drooping |
| Shape in longitudinal section: | Square |
| Shape in cross section (at level of placenta): | Angular to circular |
| Sinuation of pericarp at basal part: | Absent or very weak |
| Sinuation of pericarp excluding basal part: | Absent or very weak |
| Color at maturity: | Red and yellow striped |
| Number of locules: | Equally three and four |
| Capsaicin in placenta: | Absent |
| Fruit length: | Short |
| Fruit width: | Broad |
| Ration of length to diameter: | Medium |
| Texture of surface of fruit: | smooth or very slightly wrinkled |

-continued

| | |
|---|---|
| Glossiness of fruit: | Medium |
| Stalk cavity: | Present |
| Depth of stalk cavity: | Medium |
| Stalk length: | Medium to long |
| Stalk thickness: | Medium |
| Calyx aspect: | Non-enveloping |
| Shape of apex of fruit: | Moderately depressed |
| Depth of interloculary grooves: | Medium |
| Thickness of fruit flesh: | Medium to thick |
| Disease/Pest Resistance: | |
| Tobamovirus pathotype $P_0$: | Resistant |
| Tobamovirus pathotype $P_{1-2}$: | Resistant |
| Tobamovirus pathotype $P_{1-2-3}$: | Susceptible |
| Tobamovirus pathotype $P_1$: | Resistant |
| Potato Virus Y pathotype $P_0$: | Susceptible |

Comparisons to Most Similar Variety

Table A below compares the characteristic of the mutant pepper plant variety 'RY5' with the most similar variety, 'Healey'. Column 1 lists the characteristic, column 2 shows the characteristics for mutant pepper plant variety 'RY5', and column 3 shows the characteristics for most similar pepper variety 'Healey'.

TABLE A

| Characteristic | 'RY5' | 'Healey' |
|---|---|---|
| Mature fruit color | Red and yellow striped | Red |

DEPOSIT INFORMATION

Seed of Pepper Variety 'RY1'

A deposit of the pepper variety 'RY1' is maintained by Enza Zaden Beheer B. V., having an address at Haling 1e, 1602 DB Enkhuizen, Netherlands. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed by affording access to a deposit of at least 2,500 seeds of the same variety with the National Collection of Industrial, Food and Marine Bacteria Ltd. (NCIMB Ltd), Ferguson Building, Craibstone Estate, Bucksburn, Aberdeen, AB21 9YA, United Kingdom.

At least 2500 seeds of pepper variety 'RY1' were deposited on DATE according to the Budapest Treaty in the National Collection of Industrial, Food and Marine Bacteria Ltd. (NCIMB Ltd), Ferguson Building, Craibstone Estate, Bucksburn, Aberdeen, AB21 9YA, United Kingdom. The deposit has been assigned NCIMB number X1. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed.

The deposit will be maintained in the NCIMB depository, which is a public depository, for a period of at least 30 years, or at least 5 years after the most recent request for a sample of the deposit, or for the effective life of the patent, whichever is longer, and will be replaced if a deposit becomes nonviable during that period.

Tissue Culture of Pepper Variety 'RY1'

A deposit of tissue culture of the pepper variety 'RY1' is maintained by Enza Zaden Beheer B. V., having an address at Haling 1e, 1602 DB Enkhuizen, Netherlands. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed by affording access to the tissue culture deposit of the same variety with the National Collection of Industrial, Food and Marine Bacteria Ltd. (NCIMB Ltd), Ferguson Building, Craibstone Estate, Bucksburn, Aberdeen, AB21 9YA, United Kingdom.

Tissue culture of pepper variety 'RY1' were deposited on DATE according to the Budapest Treaty in the National Collection of Industrial, Food and Marine Bacteria Ltd. (NCIMB Ltd), Ferguson Building, Craibstone Estate, Bucksburn, Aberdeen, AB21 9YA, United Kingdom. The deposit has been assigned NCIMB number Y1. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed.

The deposit will be maintained in the NCIMB depository, which is a public depository, for a period of at least 30 years, or at least 5 years after the most recent request for a sample of the deposit, or for the effective life of the patent, whichever is longer, and will be replaced if a deposit becomes nonviable during that period.

Seed of Pepper Variety 'RY2'

A deposit of the pepper variety 'RY2' is maintained by Enza Zaden Beheer B. V., having an address at Haling 1e, 1602 DB Enkhuizen, Netherlands. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed by affording access to a deposit of at least 2,500 seeds of the same variety with the National Collection of Industrial, Food and Marine Bacteria Ltd. (NCIMB Ltd), Ferguson Building, Craibstone Estate, Bucksburn, Aberdeen, AB21 9YA, United Kingdom.

At least 2500 seeds of pepper variety 'RY2' were deposited on DATE according to the Budapest Treaty in the National Collection of Industrial, Food and Marine Bacteria Ltd. (NCIMB Ltd), Ferguson Building, Craibstone Estate, Bucksburn, Aberdeen, AB21 9YA, United Kingdom. The deposit has been assigned NCIMB number X2. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed.

The deposit will be maintained in the NCIMB depository, which is a public depository, for a period of at least 30 years, or at least 5 years after the most recent request for a sample of the deposit, or for the effective life of the patent, whichever is longer, and will be replaced if a deposit becomes nonviable during that period.

Tissue Culture of Pepper Variety 'RY2'

A deposit of tissue culture of the pepper variety 'RY2' is maintained by Enza Zaden Beheer B. V., having an address at Haling 1e, 1602 DB Enkhuizen, Netherlands. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed by affording access to the tissue culture deposit of the same variety with the National Collection of Industrial, Food and Marine Bacteria Ltd. (NCIMB Ltd), Ferguson Building, Craibstone Estate, Bucksburn, Aberdeen, AB21 9YA, United Kingdom.

Tissue culture of pepper variety 'RY2' were deposited on DATE according to the Budapest Treaty in the National Collection of Industrial, Food and Marine Bacteria Ltd. (NCIMB Ltd), Ferguson Building, Craibstone Estate, Bucksburn, Aberdeen, AB21 9YA, United Kingdom. The deposit has been assigned NCIMB number Y2. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed.

The deposit will be maintained in the NCIMB depository, which is a public depository, for a period of at least 30 years, or at least 5 years after the most recent request for a sample of the deposit, or for the effective life of the patent, whichever is longer, and will be replaced if a deposit becomes nonviable during that period.

Seed of Pepper Variety 'RY3'

A deposit of the pepper variety 'RY3' is maintained by Enza Zaden Beheer B. V., having an address at Haling 1e, 1602 DB Enkhuizen, Netherlands. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed by affording access to a deposit of at least 2,500 seeds of the same variety with the National Collection of Industrial, Food and Marine Bacteria Ltd. (NCIMB Ltd), Ferguson Building, Craibstone Estate, Bucksburn, Aberdeen, AB21 9YA, United Kingdom.

At least 2500 seeds of pepper variety 'RY3' were deposited on DATE according to the Budapest Treaty in the National Collection of Industrial, Food and Marine Bacteria Ltd. (NCIMB Ltd), Ferguson Building, Craibstone Estate, Bucksburn, Aberdeen, AB21 9YA, United Kingdom. The deposit has been assigned NCIMB number X3. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed.

The deposit will be maintained in the NCIMB depository, which is a public depository, for a period of at least 30 years, or at least 5 years after the most recent request for a sample of the deposit, or for the effective life of the patent, whichever is longer, and will be replaced if a deposit becomes nonviable during that period.

Tissue Culture of Pepper Variety 'RY3'

A deposit of tissue culture of the pepper variety 'RY3' is maintained by Enza Zaden Beheer B. V., having an address at Haling 1e, 1602 DB Enkhuizen, Netherlands. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed by affording access to the tissue culture deposit of the same variety with the National Collection of Industrial, Food and Marine Bacteria Ltd. (NCIMB Ltd), Ferguson Building, Craibstone Estate, Bucksburn, Aberdeen, AB21 9YA, United Kingdom.

Tissue culture of pepper variety 'RY3' were deposited on DATE according to the Budapest Treaty in the National Collection of Industrial, Food and Marine Bacteria Ltd. (NCIMB Ltd), Ferguson Building, Craibstone Estate, Bucksburn, Aberdeen, AB21 9YA, United Kingdom. The deposit has been assigned NCIMB number Y3. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed.

The deposit will be maintained in the NCIMB depository, which is a public depository, for a period of at least 30 years, or at least 5 years after the most recent request for a sample of the deposit, or for the effective life of the patent, whichever is longer, and will be replaced if a deposit becomes nonviable during that period.

Seed of Pepper Variety 'RY4'

A deposit of the pepper variety 'RY4' is maintained by Enza Zaden Beheer B. V., having an address at Haling 1e, 1602 DB Enkhuizen, Netherlands. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed by affording access to a deposit of at least 2,500 seeds of the same variety with the National Collection of Industrial, Food and Marine Bacteria Ltd. (NCIMB Ltd), Ferguson Building, Craibstone Estate, Bucksburn, Aberdeen, AB21 9YA, United Kingdom.

At least 2500 seeds of pepper variety 'RY4' were deposited on DATE according to the Budapest Treaty in the National Collection of Industrial, Food and Marine Bacteria Ltd. (NCIMB Ltd), Ferguson Building, Craibstone Estate, Bucksburn, Aberdeen, AB21 9YA, United Kingdom. The deposit has been assigned NCIMB number X4. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed.

The deposit will be maintained in the NCIMB depository, which is a public depository, for a period of at least 30 years, or at least 5 years after the most recent request for a sample of the deposit, or for the effective life of the patent, whichever is longer, and will be replaced if a deposit becomes nonviable during that period.

Tissue Culture of Pepper Variety 'RY4'

A deposit of tissue culture of the pepper variety 'RY4' is maintained by Enza Zaden Beheer B. V., having an address at Haling 1e, 1602 DB Enkhuizen, Netherlands. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed by affording access to the tissue culture deposit of the same variety with the National Collection of Industrial, Food and Marine Bacteria Ltd. (NCIMB Ltd), Ferguson Building, Craibstone Estate, Bucksburn, Aberdeen, AB21 9YA, United Kingdom.

Tissue culture of pepper variety 'RY4' were deposited on DATE according to the Budapest Treaty in the National Collection of Industrial, Food and Marine Bacteria Ltd. (NCIMB Ltd), Ferguson Building, Craibstone Estate, Bucksburn, Aberdeen, AB21 9YA, United Kingdom. The deposit has been assigned NCIMB number Y4. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed.

The deposit will be maintained in the NCIMB depository, which is a public depository, for a period of at least 30 years, or at least 5 years after the most recent request for a sample of the deposit, or for the effective life of the patent, whichever is longer, and will be replaced if a deposit becomes nonviable during that period.

Seed of Pepper Variety 'RY5'

A deposit of the pepper variety 'RY5' is maintained by Enza Zaden Beheer B. V., having an address at Haling 1e, 1602 DB Enkhuizen, Netherlands. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed by affording access to a deposit of at least 2,500 seeds of the same variety with the National Collection of Industrial, Food and Marine Bacteria Ltd. (NCIMB Ltd), Ferguson Building, Craibstone Estate, Bucksburn, Aberdeen, AB21 9YA, United Kingdom.

At least 2500 seeds of pepper variety 'RY5' were deposited on DATE according to the Budapest Treaty in the National Collection of Industrial, Food and Marine Bacteria Ltd. (NCIMB Ltd), Ferguson Building, Craibstone Estate, Bucksburn, Aberdeen, AB21 9YA, United Kingdom. The deposit has been assigned NCIMB number X5. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed.

The deposit will be maintained in the NCIMB depository, which is a public depository, for a period of at least 30 years, or at least 5 years after the most recent request for a sample of the deposit, or for the effective life of the patent, whichever is longer, and will be replaced if a deposit becomes nonviable during that period.

Tissue Culture of Pepper Variety 'RY5'

A deposit of tissue culture of the pepper variety 'RY5' is maintained by Enza Zaden Beheer B. V., having an address at Haling 1e, 1602 DB Enkhuizen, Netherlands. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed by affording access to the tissue culture deposit of the same variety with the National Collection of Industrial, Food and Marine Bacteria Ltd. (NCIMB Ltd), Ferguson Building, Craibstone Estate, Bucksburn, Aberdeen, AB21 9YA, United Kingdom.

Tissue culture of pepper variety 'RY5' were deposited on DATE according to the Budapest Treaty in the National Collection of Industrial, Food and Marine Bacteria Ltd. (NCIMB Ltd), Ferguson Building, Craibstone Estate, Bucksburn, Aberdeen, AB21 9YA, United Kingdom. The deposit has been assigned NCIMB number Y5. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed.

The deposit will be maintained in the NCIMB depository, which is a public depository, for a period of at least 30 years, or at least 5 years after the most recent request for a sample of the deposit, or for the effective life of the patent, whichever is longer, and will be replaced if a deposit becomes nonviable during that period.

Seed of Pepper Variety 'Maduro'

A deposit of the pepper variety 'Maduro' is maintained by Enza Zaden Beheer B. V., having an address at Haling 1e, 1602 DB Enkhuizen, Netherlands. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed by affording access to a deposit of at least 2,500 seeds of the same variety with the National Collection of Industrial, Food and Marine Bacteria Ltd. (NCIMB Ltd), Ferguson Building, Craibstone Estate, Bucksburn, Aberdeen, AB21 9YA, United Kingdom.

At least 2500 seeds of pepper variety 'Maduro' were deposited on DATE according to the Budapest Treaty in the National Collection of Industrial, Food and Marine Bacteria Ltd. (NCIMB Ltd), Ferguson Building, Craibstone Estate, Bucksburn, Aberdeen, AB21 9YA, United Kingdom. The deposit has been assigned NCIMB number X6. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed.

The deposit will be maintained in the NCIMB depository, which is a public depository, for a period of at least 30 years, or at least 5 years after the most recent request for a sample of the deposit, or for the effective life of the patent, whichever is longer, and will be replaced if a deposit becomes nonviable during that period.

Seed of Pepper Variety 'Marinello'

A deposit of the pepper variety 'Marinello' is maintained by Enza Zaden Beheer B. V., having an address at Haling 1e, 1602 DB Enkhuizen, Netherlands. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed by affording access to a deposit of at least 2,500 seeds of the same variety with the National Collection of Industrial, Food and Marine Bacteria Ltd. (NCIMB Ltd), Ferguson Building, Craibstone Estate, Bucksburn, Aberdeen, AB21 9YA, United Kingdom.

At least 2500 seeds of pepper variety 'Maranello' were deposited on DATE according to the Budapest Treaty in the National Collection of Industrial, Food and Marine Bacteria Ltd. (NCIMB Ltd), Ferguson Building, Craibstone Estate, Bucksburn, Aberdeen, AB21 9YA, United Kingdom. The deposit has been assigned NCIMB number X7. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed.

The deposit will be maintained in the NCIMB depository, which is a public depository, for a period of at least 30 years, or at least 5 years after the most recent request for a sample of the deposit, or for the effective life of the patent, whichever is longer, and will be replaced if a deposit becomes nonviable during that period.

Seed of Pepper Variety 'Healey'

A deposit of the pepper variety 'Healey' is maintained by Enza Zaden Beheer B. V., having an address at Haling 1e, 1602 DB Enkhuizen, Netherlands. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed by affording access to a deposit of at least 2,500 seeds of the same variety with the National Collection of Industrial, Food and Marine Bacteria Ltd. (NCIMB Ltd), Ferguson Building, Craibstone Estate, Bucksburn, Aberdeen, AB21 9YA, United Kingdom.

At least 2500 seeds of pepper variety 'Healey' were deposited on DATE according to the Budapest Treaty in the National Collection of Industrial, Food and Marine Bacteria Ltd. (NCIMB Ltd), Ferguson Building, Craibstone Estate, Bucksburn, Aberdeen, AB21 9YA, United Kingdom. The deposit has been assigned NCIMB number X8. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed.

The deposit will be maintained in the NCIMB depository, which is a public depository, for a period of at least 30 years, or at least 5 years after the most recent request for a sample of the deposit, or for the effective life of the patent, whichever is longer, and will be replaced if a deposit becomes nonviable during that period.

The present disclosure will be more fully understood by reference to the following Examples. They should not, however, be construed as limiting the scope of the present disclosure.

EXAMPLES

Example 1: Identification and Characterization of RY1 Pepper Plant

Pepper is an important and valuable field crop, and there is a continued need for developing new and interesting hybrid peppers. To this end, an inbred pepper plant that produces yellow fruit (pepper variety 'OP.1745') and an inbred pepper plant that produces red fruit (pepper variety 'OP.2023') were crossed, and the resulting seeds were planted to create a population of $F_1$ hybrid plants. The resulting $F_1$ hybrid plants, commercially available as pepper variety 'Maduro', were grown, and a selection process was initiated to identify mutant plants that produced fruit with alternating yellow and red stripes or patches ('Maduro' produces uniform, single-colored red fruit when mature).

Figure 2:
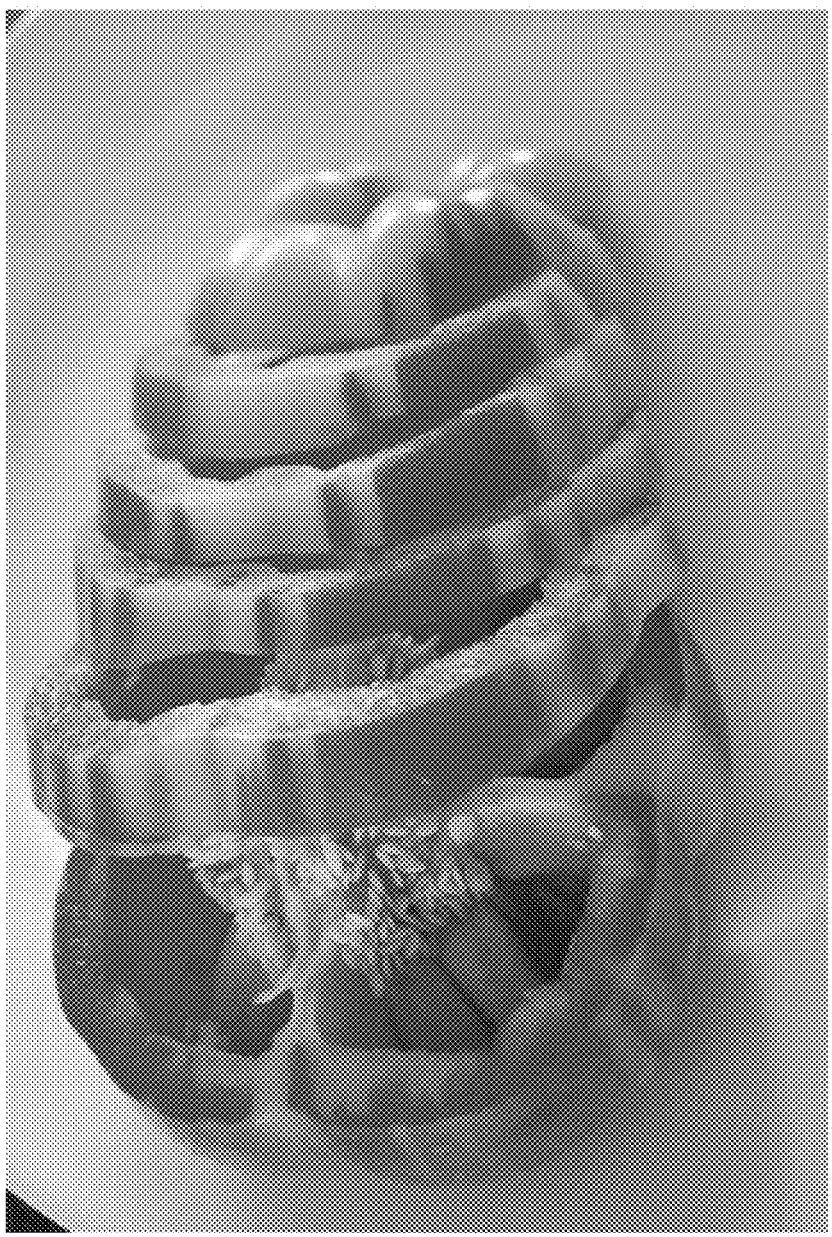
FIG. 2 shows slices of a yellow and red striped fruit of a chimeric pepper plant (RY1).

One of these mutant plants (RY1) was selected for further characterization. This plant produced fruit with alternating, irregular yellow and red stripes/patches, with each fruit having a unique color pattern (FIG. 1). The irregular fruit color distribution pattern was also observed across the fruit wall from outside to inside, and the outside and inside of the fruit could have the same or different coloring (FIG. 2). Aside from the unique coloring of the fruit, RY1 was phenotypically identical to 'Maduro'. Interestingly, while selfing progeny of 'Maduro' segregated for fruit color in a typical Mendelian 3:1 (red to yellow) ratio, selfing progeny of RY1 did not segregate in a typical Mendelian ratio, only bearing off-type, uniformly yellow fruit.

Figure 3:
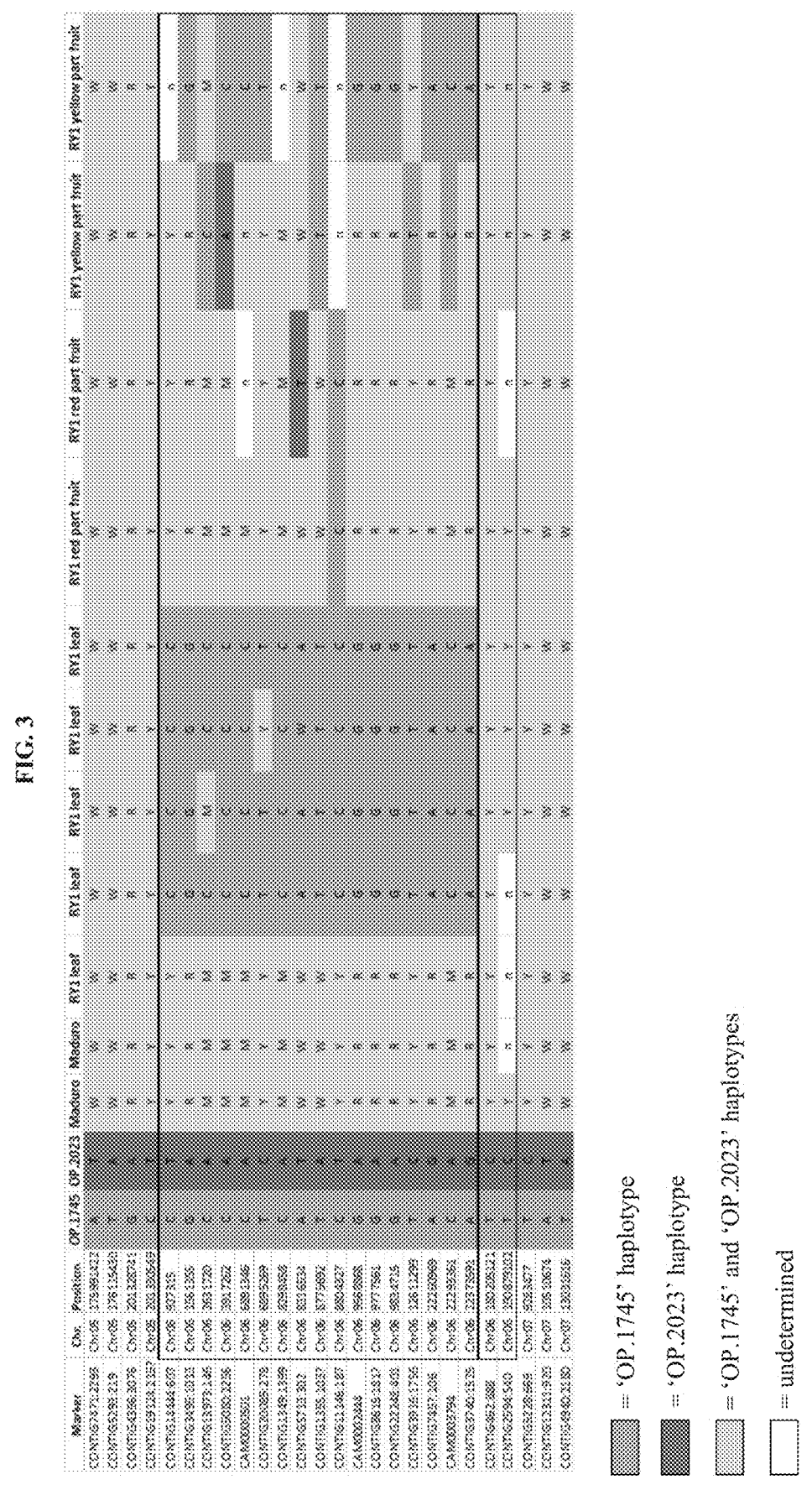

To further characterize the RY1 plants, DNA marker profiles were generated for the inbred parent plants 'OP.1745' and 'OP.2023', 'Maduro', and RY1, using markers distributed over all 12 chromosomes of the plants. To gain a clearer understanding of the genetic profile of RY1, marker profiles were generated for multiple leaf tissues, as well as multiple portions of both the yellow and red parts of the fruit. Interestingly, the marker profile for some of the portions of RY1 (e.g., the portions taken from the red part of the fruit) were identical to 'Maduro', while the marker profile for other portions of RY1 (e.g., the portions taken from the yellow part of the fruit, and some, but not all, of the leaf samples) showed an aberrant profile with respect to the markers located on the upper portion of chromosome six, between base pair positions 927,315 and 22,373,591 (FIG. 3). At these positions, the marker profiles were similar to the marker profiles for 'OP.1745' (the inbred parent pepper plant that produces yellow fruit), and not 'Maduro'. Markers at positions 180,205,121 and 190,879,102 on chromosome six were identical to 'Maduro' for all tissues tested. Without wishing to be bound by theory, these data suggested that some of the tissues of RY1 had lost the upper portion of chromosome six that was derived from 'OP.2023' (the inbred parent pepper plant that produces red fruit), indicating that these tissues may have been hemizygous for the upper portion of chromosome six.

The Capsanthin-Capsorubin Synthase (CCS) gene provides peppers with their color (See e.g., Thorup, T. A. et al. Proc. Natl. Acad. Sci. USA. 2000 Oct. 10; 97(21):11192-7). Red or yellow fruit color is determined by the presence or absence of a functional CCS gene, respectively. The CCS gene is located on the upper portion of chromosome six, between base pair positions 927,315 and 22,373,591. The yellow allele at the CCS locus harbors C to A and T to C polymorphisms in the nucleic acid encoding the 3' UTR of the CCS transcript, and a marker, CAM000413, is able to detect these polymorphisms (FIG. 4). The CAM000413 marker was used to identify the alleles of the CCS locus in 9 samples (3 independent samples of each organ/tissue from 3 plants) of various organ/tissue types for both 'Maduro' and RY1 plants. Table 1 describes the results of this analysis.

TABLE 1

CAM000413 marker analysis for tissues from 'Maduro' and RY1

| | 'Maduro' | | | RY1 | | |
|---|---|---|---|---|---|---|
| Tissue | Yellow allele only | Red and yellow alleles | Red allele only | Yellow allele only | Red and yellow alleles | Red allele only |
| Seed | 0 | 9 | 0 | 9 | 0 | 0 |
| Epidermal peel fruit | 0 | 9 | 0 | 9 | 0 | 0 |
| Filament | 0 | 9 | 0 | 7 | 2 | 0 |
| Pericarp | 0 | 9 | 0 | 6 (yellow part) | 3 (red part) | 0 |
| Septum | 0 | 9 | 0 | 9 | 0 | 0 |
| Placenta | 0 | 9 | 0 | 1 | 8 | 0 |
| Sepal | 0 | 9 | 0 | 6 | 3 | 0 |
| Petal | 0 | 9 | 0 | 8 | 1 | 0 |
| Ovary | 0 | 9 | 0 | 4 | 5 | 0 |
| Anther | 0 | 9 | 0 | 1 | 8 | 0 |
| Leaf - middle part | 0 | 9 | 0 | 8 | 1 | 0 |
| Leaf - side part | 0 | 9 | 0 | 9 | 0 | 0 |
| vascular | 0 | 9 | 0 | 5 | 3 | 0 |
| Stem | 0 | 9 | 0 | 5 | 4 | 0 |

As expected, all 9 samples of each of the organ/tissue types tested for 'Maduro' contained both a red and yellow allele at the CCS locus. In contrast to 'Maduro', some of the organ/tissue types of RY1 contained both a red and yellow allele at the CCS locus (e.g., the anther and placenta tissues), while other tissue/organ types appeared to only contain a yellow allele at the CCS locus (e.g., the epidermal peel, filament, septum, petal, and leaf parts tissues). Additionally, some organ/tissue types tested were a more even distribution of containing both a red and yellow allele at the CCS locus, and only a yellow allele at this locus (e.g., the pericarp, sepal, ovary, vascular and stem tissues). Interestingly, the 9 seed samples taken from RY1 only contained the yellow allele at the CCS locus. Taken together, these results revealed that the RY1 plant was a chimeric pepper plant having some tissues containing both the yellow and red allele at the CCS locus, and other tissues with only the yellow allele at the CCS locus.

Example 2: Identification and Characterization of RY2 Pepper Plant

Figure 5:
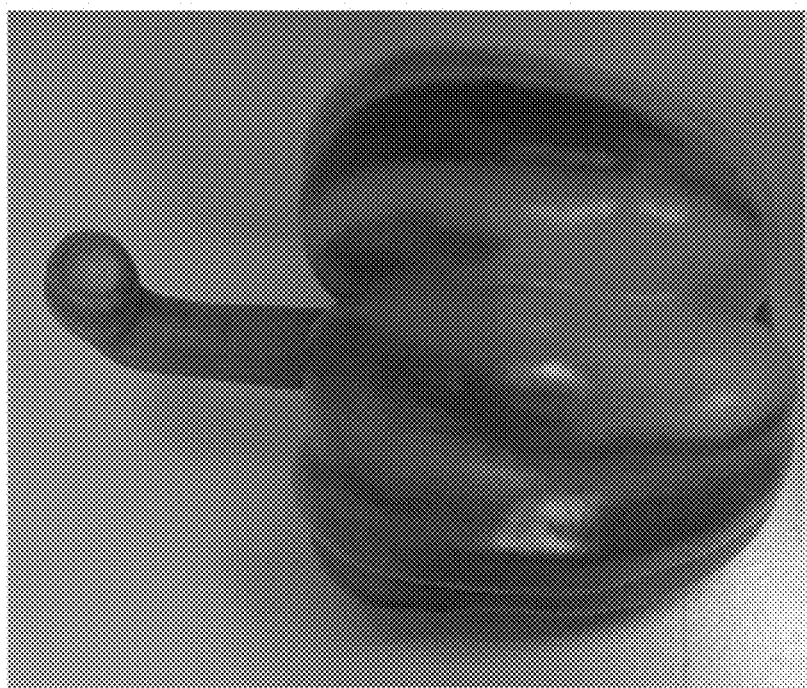
FIG. 5 shows a side view of a yellow and red striped fruit of a chimeric pepper plant (RY2).

Field trials were initiated to identify other inbred pepper plant crosses that would give rise to mutant $F_1$ hybrid pepper plants that produce yellow and red striped, patched or variegated pepper fruit. As such, an inbred pepper plant that produces yellow fruit (pepper variety 'OP.1745') and an inbred pepper plant that produces red fruit (pepper variety 'OP.1755') were crossed, and the resulting seeds were planted to create a population of $F_1$ hybrid plants. The resulting $F_1$ hybrid plants, commercially available as pepper variety 'Marinello', were grown, and a selection process was initiated to identify mutant plants of this $F_1$ hybrid that produced fruit with alternating yellow and red stripes or patches ('Marinello' produces uniform, single-colored red fruit when mature). Another mutant $F_1$ hybrid plant (RY2) was found to produce yellow and red striped/patched pepper fruit. This plant produced fruit with alternating, irregular yellow and red stripes/patches (FIG. 5), similar to the fruit produced by RY1. Similar to the experiments described above, the CAM000413 marker was used to identify the alleles of the CCS locus in four samples of red and yellow pericarp tissue obtained from the fruit of the RY2 plants. Table 2 describes the results of this analysis.

TABLE 2

CAM000413 marker analysis for tissues from RY2

| | RY2 | | | |
|---|---|---|---|---|
| Tissue | Yellow allele only | Red and yellow alleles | Red allele only | Undetermined |
| Pericarp | 1 (yellow part) | 3 (red part) 1 (yellow part) | 0 | 1 (red part) 2 (yellow part) |

Three of the four samples taken from the red portion of the pericarp tissue contained the CAM000413 marker for both the red and yellow alleles, and one of the four samples taken from the yellow portion of the pericarp tissue contained the CAM000413 marker for only the yellow allele, in agreement with the results observed for sample from RY1 (Table 1 above). Unexpectedly, one of the four samples taken from the yellow tissue contained the CAM000413 marker for both the red and yellow alleles, and no reliable results could be obtained for the other yellow pericarp samples. This suggests that there may have been cross contamination from the red portion of the pericarp tissue in the yellow samples, or the DNA quality of the samples was low.

A more extensive analysis of the CAM000413 marker was used to identify the alleles of the CCS locus in 9 samples (3 independent samples of each organ/tissue from 3 plants) of various organ/tissue types for both 'Maranello' and RY2 plants to better understand these plants. Table 3 describes the results of this analysis.

TABLE 3

CAM000413 marker analysis for tissues from 'Maranello' and RY2

| | 'Maranello' | | | RY2 | | |
|---|---|---|---|---|---|---|
| Tissue | Yellow allele only | Red and yellow alleles | Red allele only | Yellow allele only | Red and yellow alleles | Red allele only |
| Seed | 0 | 9 | 0 | 1 | 8 | 0 |
| Epidermal peel fruit | 0 | 9 | 0 | 0 | 9 | 0 |
| Filament | 0 | 9 | 0 | 0 | 9 | 0 |
| Pericarp | 0 | 9 | 0 | 5 (Yellow part) | 4 (Red part) | 0 |
| Septum | 0 | 9 | 0 | 0 | 9 | 0 |
| Placenta | 0 | 9 | 0 | 0 | 9 | 0 |
| Sepal | 0 | 9 | 0 | 0 | 9 | 0 |
| Petal | 0 | 9 | 0 | 0 | 9 | 0 |
| Ovary | 0 | 9 | 0 | 0 | 9 | 0 |
| Anther | 0 | 9 | 0 | 0 | 9 | 0 |
| Leaf - middle part | 0 | 9 | 0 | 0 | 9 | 0 |
| Leaf - side part | 0 | 9 | 0 | 1 | 8 | 0 |
| vascular | 0 | 9 | 0 | 0 | 9 | 0 |
| Stem | 0 | 9 | 0 | 0 | 9 | 0 |

Similar to what was observed for 'Maduro' and RY1, all tissue samples of 'Maranello' contain both the red and the yellow allele at the CCs locus, whereas in RY2 some samples show only the yellow allele and others both the yellow and the red alleles in different tissues.

Example 3: Identification and Characterization of RY3 Pepper Plant

A third mutant pepper plant was identified that produced yellow and red striped/patched/variegated pepper fruit (RY3). This pepper plant was a mutant of an $F_1$ hybrid pepper plant, commercially available as pepper variety 'Waltz'. Table 4 shows marker analysis performed on the $F_1$ hybrid plants 'Waltz', 'Maduro', and 'Maranello', as well as the parental plants of 'Maduro' and 'Maranello' ('OP.1745', 'OP.2023', and 'OP.1755').

TABLE 4A

Marker analysis of $F_1$ hybrid and parental pepper plants

| | Marker (CAM0000) | | | | | | | | | | | | |
|---|---|---|---|---|---|---|---|---|---|---|---|---|---|
| Plant: | 402 | 408 | 413 | 442 | 448 | 450 | 459 | 468 | 469 | 471 | 472 | 473 | 491 |
| 'OP.2023' | 0202 | 0202 | 0101 | 0202 | 0101 | 0101 | 0202 | 0202 | 0202 | 0202 | 0202 | 0101 | 0202 |
| 'OP.1745' | 0101 | 0202 | 0202 | 0101 | 0202 | 0202 | 0202 | 0101 | 0202 | 0101 | 0202 | 0202 | 0505 |
| 'Maduro' | 0102 | 0202 | 0102 | 0102 | 0102 | 0102 | 0202 | 0102 | 0202 | 0102 | 0202 | 0102 | 0205 |
| 'OP.1755' | 0202 | 0202 | 0101 | 0101 | 0101 | 0101 | 0202 | 0202 | 0202 | 0202 | 0202 | 0101 | 0202 |
| 'OP.1745' | 0101 | 0202 | 0202 | 0101 | 0202 | 0202 | 0202 | 0101 | 0202 | 0101 | 0202 | 0202 | 0505 |
| 'Maranello' | 0102 | 0202 | 0102 | 0101 | 0102 | 0102 | 0202 | 0102 | 0202 | 0102 | 0202 | 0102 | 0205 |
| 'Waltz' | 0202 | 0202 | 0102 | 0202 | 0101 | 0102 | 0202 | 0102 | 0202 | 0202 | 0202 | 0202 | 9999 |

0101 = homozygous for allele 1

0202 = homozygous for allele 2

0102 = heterozygous for allele 1 and 2

0505 = homozygous for allele 5

9999 = unknown marker score

As indicated by the marker analysis in Table 4, the $F_1$ hybrid pepper plant 'Waltz' did not share common parent plants with either 'Maduro' or 'Maranello', suggesting that the mutant pepper plant derived from 'Waltz' was yet another distinctive pepper plant that produced yellow and red striped fruit.

An analysis of the CAM000413 marker was used to identify the alleles of the CCS locus in 9 samples (3 independent samples of each organ/tissue from 3 plants) of various organ/tissue types for both 'Waltz' and RY3 plants. Table 4B describes the results of this analysis.

TABLE 4B

CAM000413 marker analysis for tissues from 'Waltz' and RY3

| | 'Waltz' | | | RY3 | | |
|---|---|---|---|---|---|---|
| Tissue | Yellow allele only | Red and yellow alleles | Red allele only | Yellow allele only | Red and yellow alleles | Red allele only |
| Seed | 0 | 9 | 0 | 1 | 8 | 0 |
| Epidermal peel fruit | 0 | 9 | 0 | 3 | 6 | 0 |
| Filament | 0 | 9 | 0 | 4 | 5 | 0 |
| Pericarp | 0 | 9 | 0 | 4 (yellow part) | 5 (red part) | 0 |
| Septum | 0 | 9 | 0 | 6 | 3 | 0 |
| Placenta | 0 | 9 | 0 | 0 | 9 | 0 |
| Sepal | 0 | 9 | 0 | 8 | 1 | 0 |
| Petal | 0 | 9 | 0 | 4 | 5 | 0 |
| Ovary | 0 | 9 | 0 | 0 | 9 | 0 |
| Anther | 0 | 9 | 0 | 9 | 0 | 0 |
| Leaf - middle part | 0 | 9 | 0 | 8 | 1 | 0 |
| Leaf - side part | 0 | 9 | 0 | 7 | 2 | 0 |
| vascular | 0 | 9 | 0 | 2 | 6 | 0 |
| Stem | 0 | 9 | 0 | 0 | 9 | 0 |

Similar to what was observed for 'Maduro' and RY1, all tissue samples of 'Wlatz' contain both the red and the yellow allele at the CCs locus, whereas in RY3 some samples show only the yellow allele and others both the yellow and the red alleles in different tissues.

Example 4: Identification and Characterization of RY4 Pepper Plant

Figure 6:
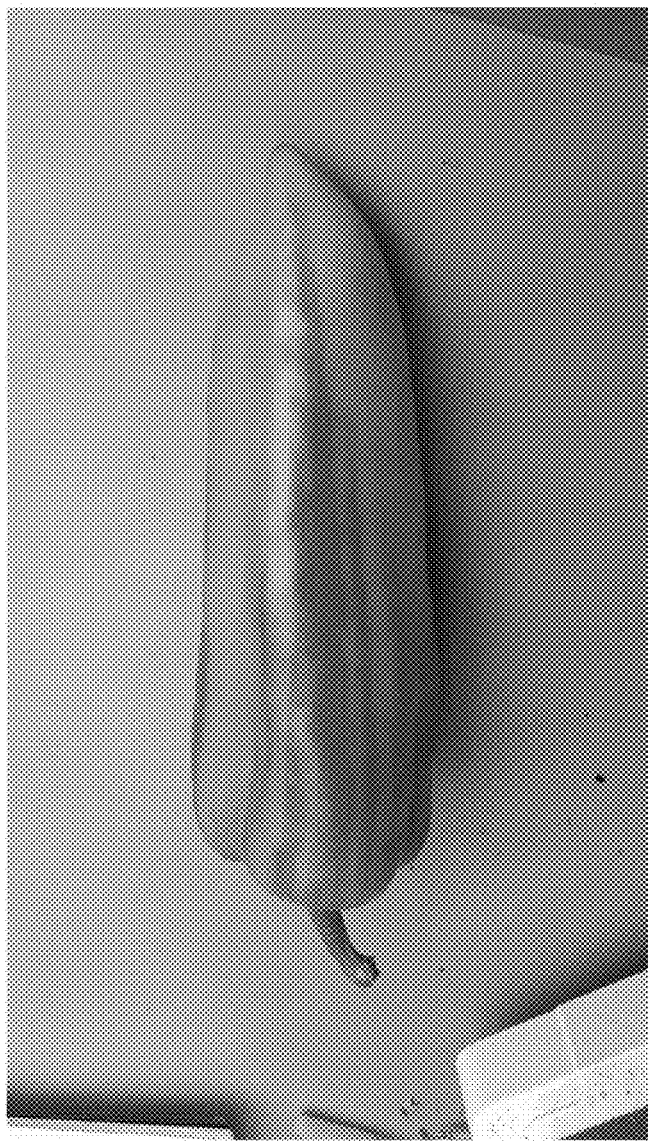
FIG. 6 shows a side view of a yellow and red striped fruit of a chimeric pepper plant (RY4).
Figure 7B:
FIGS. 7A-7D shows several yellow and red striped fruit of a chimeric pepper plant (RY5), as well as unripened fruit.
Figure 7A:
Figure 7C:
Figure 7D:

A fourth mutant pepper plant was identified that produced yellow and red striped/patched/variegated pepper fruit (RY4). This pepper was an $F_3$ hybrid pepper derived from a breeding scheme using a proprietary parental pepper line that produced red fruit ('Rubinex'דOP.1091'×OP.1747') crossed with a proprietary parental pepper line that produced yellow fruit ('OP.1033×(Br CTx378)×'Ramiro). $F_3$ hybrid plants were produced from this breeding scheme, the resulting $F_3$ hybrid plants were grown, and a selection process was initiated to identify mutant plants that produced fruit with alternating yellow and red stripes or patches. One of these mutant plants (RY4) produced fruit with alternating, irregular yellow and red stripes/patches (FIG. 6).

Example 5: Identification and Characterization of RY5 Pepper Plant

A fifth mutant pepper plant was identified that produced yellow and red striped/patched/variegated pepper fruit (RY5). A pepper plant variety that produces yellow fruit (pepper variety 'OP.1745') and a pepper plant variety that produces red fruit (pepper variety 'OP.0900') were crossed, and the resulting seeds were planted to create a population of $F_1$ hybrid plants. The resulting $F_1$ hybrid plants, commercially available as pepper variety 'Healey', were grown, and a selection process was initiated to identify mutant plants that produced fruit with alternating yellow and red stripes or patches. One of these mutant plants (RY5) produced fruit with alternating, irregular yellow and red stripes/patches (FIG. 7A-D). Table 5 shows marker analysis performed on the $F_1$ hybrid plants 'Healey', as well as the parental plants of 'Healy' ('OP.1745' and 'OP.0900').

TABLE 5

Marker analysis of $F_1$ hybrid and parental pepper plants

| | Marker (CAM0000) | | | | | | | | | | | | |
|---|---|---|---|---|---|---|---|---|---|---|---|---|---|
| Plant: | 402 | 408 | 413 | 442 | 448 | 450 | 459 | 468 | 469 | 471 | 472 | 473 | 491 |
| 'OP.0900' | 0202 | 0202 | 0101 | 0101 | 0101 | 0101 | 0202 | 0202 | 0202 | 0202 | 0202 | 0101 | 0202 |
| 'OP.1745' | 0101 | 0202 | 0202 | 0101 | 0202 | 0202 | 0202 | 0101 | 0202 | 0101 | 0202 | 0202 | 0505 |
| 'Healey' | 0102 | 0202 | 0102 | 0101 | 0102 | 0102 | 0202 | 0102 | 0202 | 0102 | 0202 | 0102 | 0205 |

0101 = homozygous for allele 1
0202 = homozygous for allele 2
0102 = heterozygous for allele 1 and 2
0505 = homozygous for allele 5
9999 = unknown marker score An analysis of the CAM000413 marker was used to identify the alleles of the CCS locus in 9 samples (3 independent samples of each organ/tissue from 3 plants) of various organ/tissue types for both 'Healey' and RY5 plants. Table 6 describes the results of this analysis.

TABLE 6

CAM000413 marker analysis for tissues from 'Healey' and RY5

| | 'Healey' | | | RY5 | | |
|---|---|---|---|---|---|---|
| Tissue | Yellow allele only | Red and yellow alleles | Red allele only | Yellow allele only | Red and yellow alleles | Red allele only |
| Seed | 0 | 9 | 0 | 6 | 3 | 0 |
| Epidermal peel fruit | 0 | 9 | 0 | 5 | 4 | 0 |
| Filament | 0 | 9 | 0 | 0 | 9 | 0 |
| Pericarp | 0 | 9 | 0 | 4 (yellow part) | 5 (red part) | 0 |
| Septum | 0 | 9 | 0 | 7 | 2 | 0 |
| Placenta | 0 | 9 | 0 | 0 | 9 | 0 |
| Sepal | 0 | 9 | 0 | 8 | 1 | 0 |
| Petal | 0 | 9 | 0 | 3 | 6 | 0 |
| Ovary | 0 | 9 | 0 | 1 | 8 | 0 |
| Anther | 0 | 9 | 0 | 7 | 2 | 0 |
| Leaf - middle part | 0 | 9 | 0 | 8 | 1 | 0 |
| Leaf - side part | 0 | 9 | 0 | 9 | 0 | 0 |
| vascular | 0 | 9 | 0 | 1 | 8 | 0 |
| Stem | 0 | 9 | 0 | 0 | 9 | 0 |

Similar to what was observed for 'Maduro' and RY1, all tissue samples of 'Healey' contain both the red and the yellow allele at the CCs locus, whereas in RY5 some samples show only the yellow allele and others both the yellow and the red alleles in different tissues.

Example 6: Vegetative Propagation of RY1 Chimeric Pepper Plant

The yellow and red striped pepper phenotype was not found in the progeny of the RY1 chimeric pepper plant. As indicated in Table 1, the seeds produced from these plants only contained the yellow allele at the CCS locus, and peppers produced by plants grown from these seeds always bore off-type, uniformly yellow fruit. The yellow and red striped pepper phenotype was found, nonetheless, in plants produced via cuttings from the RY1 chimeric pepper plant. However, the yellow and red pepper phenotype was somewhat unstable, as some main or side branches would spontaneously bear only off-type, uniformly yellow fruit. Once a branch bore one off-type, uniformly yellow fruit, all subsequent fruit born on that branch were off-type, uniformly yellow. The frequency with which cuttings resulted in plants with off-type producing branches ranged from 5-35%. As such, experiments were conducted to determine whether propagating particular plant material via cuttings could reduce or mitigate the number/frequency of plants with branches bearing off-type, yellow fruit.

To this end, cuttings were taken from the main branch, as well as lateral (sympodial branching) and axillary shoots, and the cuttings were vegetatively propagated. Next, the number of plants producing off-type, uniformly yellow fruit was assessed. Vegetatively propagated plants derived from axillary shoots produced a high frequency (25-35%) of plants producing off-type fruit, while surprisingly, vegetatively propagated plants derived from lateral shoots had a much lower frequency (5-15%) of plants producing off-type, uniformly yellow fruit. Additionally, vegetatively propagated plants from main branch material showed a low frequency of plants producing off-type fruit. These results suggested that vegetatively propagating plants by cuttings from the main branch or lateral shoots could reduce the frequency of off-type plants, with lateral shoots providing an unexpected 1.7 to 7 fold reduction in off-type plants when compared to axillary shoots.

Example 7: Vegetatively Propagating Plant Material Based on Marker Analysis

Another method of reducing the number of plants producing off-type, uniformly yellow fruit during vegetative propagation is to perform marker analysis on the plant material. Cuttings are taken from a chimeric plant producing yellow and red striped pepper fruit, and the plant material is subjected to marker analysis. Any marker capable of detecting a genetic difference (e.g., a single nucleotide polymorphism (SNP) at one or more chromosomal locations) between the parental plants located on chromosome six is used (e.g., CCS locus-linked markers). Plant material that is heterozygous for the tested positons (i.e., carries chromosome six from both parental plants) is selected, as this material gives the highest likelihood of propagating plants that produce yellow and red striped/patched pepper fruit. Plant material that is not heterozygous at the tested positions is discarded, as this material gives rise to plants that produce off-type, uniformly yellow fruit.

While any one or more plant materials may be tested and propagated when giving a heterozygous marker profile for chromosome six as described above, anthers provide a robust and reliable source of plant material that diminishes the frequency of producing off-type plants. Anthers are tested at the stage when the first flowers appear on the branches. Marker analysis is performed on the anther tissue, and anthers that are not heterozygous for the tested positons on chromosome six indicate a branch that will not produce yellow and red striped fruit. Cuttings from these branches may be discarded. Anthers that are heterozygous for the tested positons on chromosome six indicate a branch that will produce yellow and red striped fruit, and Cuttings from these branches may be used for vegetative propagation. Using this protocol can reduce the number/frequency of plants producing off-type fruit, producing more true-to-type plants.

Example 8: Propagating Chimeric Pepper Plants Via the BBM Method

An additional method to propagate pepper plants producing pepper fruit having a red and yellow striped color is to regenerate plants from somatic embryos generated from chimeric pepper plants. To this end, a chimeric pepper plant producing pepper fruit having a red and yellow striped color is transformed with a vector to ectopically express the transcription factor BABY BOOM AP2/ERF from *Brassica napus* (See e.g., Heidmann et al. Plant Cell Rep 30:1107-1115 and/or WO2011003471). Transient activation of BABY BOOM in the progeny plants induces cell regeneration and is used to produce somatic embryos. Pepper plants are then regenerated from the somatic embryos produced from the transformed chimeric pepper plants (See e.g., Heidmann 2015 PhD thesis Wageningen Agricultural University ISBN 978-94-6257-466-3). These pepper plants, regenerated using the BBM transformation protocol, produce pepper fruit having a yellow and red striped color.

What is claimed is:

1. A method of selecting a chimeric pepper plant that produces pepper fruit having yellow and red striped color, the method comprising:
   a) crossing a first pepper plant comprising two copies of a first allele at a Capsanthin-Capsorubin Synthase (CCS) locus, wherein the first allele comprises SEQ ID NO: 4, with a second pepper plant comprising a second allele at the CCS locus, wherein the second allele comprises SEQ ID NO: 5, to create F1 hybrid progeny;
   b) growing the F1 hybrid progeny to produce a population of F1 hybrid progeny plants; and
   c) selecting an F1 hybrid progeny plant from the population of F1 hybrid progeny plants,
   wherein the selected F1 hybrid progeny plant comprises one or more first tissues comprising only the second allele at the CCS locus,
   wherein the selected F1 hybrid progeny plant produces pepper fruit having yellow and red striped color.

2. The method of claim 1, wherein the selection comprises screening plant material from the population of F1 hybrid progeny plants to identify plants comprising one or more first tissues comprising only the second allele at the CCS locus.

3. The method of claim 1, wherein the first pepper plant produces red pepper fruit and the second pepper plant produces yellow pepper fruit.

4. The method of claim 2, wherein the plant material is selected from the group consisting of leaf material, epidermal peel material, septum material, and any combination thereof.

5. The method of claim 2, wherein the screening comprises single nucleotide polymorphism (SNP) analysis, and wherein the second allele is identified by a C at a position corresponding to nucleotide 49 of SEQ ID NO: 5 and an A at a position corresponding to nucleotide 85 of SEQ ID NO: 5.

6. The method of claim 1, wherein the selected F1 hybrid progeny plant further comprises one or more second tissues comprising the first allele and the second allele.

7. The method of claim 6, wherein the one or more first tissues is selected from the group consisting of epidermal peel, septum, sepal, anther, and leaf tissue.

8. The method of claim 7, wherein the one or more second tissues is selected from the group consisting of filament, placenta, petal, ovary, vascular, and stem tissue.

9. The method of claim 1, wherein the selected F1 hybrid progeny plant produces chimeric pericarp having one or more regions having a yellow color and comprising only the second allele and one or more regions having a red color and comprising the first allele.

* * * * *

SEQUENCE LISTING

<160> NUMBER OF SEQ ID NOS: 5

<210> SEQ ID NO 1
<211> LENGTH: 1756
<212> TYPE: DNA
<213> ORGANISM: Capsicum annuum

<400> SEQUENCE: 1

| | | | | | |
|---|---|---|---|---|---|
| ttttttttca | ctatactata | tcacctcctc | tcataaatag | ccattataaa | tcttgcattt | 60 |
| tctctaatgg | aaaccttct | aaagccttt | ccatctcctt | tactttccat | tcctactcct | 120 |
| aacatgtata | gtttcaaaca | caactccact | tttccaaatc | caaccaaaca | aaaagattca | 180 |
| agaaagttcc | attatagaaa | caaaagcagt | acacatttt | gtagctttct | tgatttagca | 240 |
| cccacatcaa | agccagagtc | tttagatgtt | aacatctcat | gggttgatac | tgatctggac | 300 |
| ggggctgaat | tcgacgtgat | catcattgga | actggccctg | ccgggcttcg | gctagctgaa | 360 |
| caagtttcta | aatatggtat | taaggtatgt | tgcgttgacc | cttcaccact | ttccatgtgg | 420 |
| ccaaataatt | atggtgtttg | ggttgatgag | tttgaaaagt | tgggattaga | agattgtcta | 480 |
| gatcataagt | ggcctgtgag | ttgtgttcat | ataagtgatc | acaagactaa | gtatttggac | 540 |
| agaccatatg | gtagagtaag | tagaaagaag | ttgaagttga | aattgttgaa | tagttgtgtt | 600 |
| gaaaatagag | tgaagtttta | taaagccaag | gttttgaaag | tgaagcatga | agaatttgag | 660 |
| tcttcgattg | tttgtgatga | tggtaggaag | ataagcggta | gcttgattgt | tgatgcaagt | 720 |
| ggctatgcta | gtgatttat | agagtatgac | aagccaagaa | accatggtta | tcaagttgct | 780 |
| catgggattt | tagcagaagt | tgataatcat | ccatttgatt | tggataaaat | gatgcttatg | 840 |
| gattggaggg | attctcattt | aggtaatgag | ccatatctga | gggtgaagaa | tactaaagaa | 900 |
| ccaacattct | tgtatgcaat | gccatttgat | aggaatttgg | tattcttgga | agagacttct | 960 |
| ttagtgagtc | ggcctatgtt | atcgtatatg | gaagtgaaaa | gaaggatggt | agcaagatta | 1020 |
| agacatttgg | ggatcaaagt | gagaagtgtc | cttgaggaag | agaagtgtgt | gatcactatg | 1080 |
| ggaggaccac | ttccgcggat | tcctcaaaat | gttatggcta | ttggtgggac | ttcagggata | 1140 |
| gttcatccat | cgtctgggta | catggtggct | cgtagcatgg | cattggcacc | agtactggct | 1200 |
| gaggccatcg | tcgaaagcct | tggctcaaca | agaatgataa | gagggtctca | actttaccat | 1260 |
| agagtttgga | atggtttgtg | gccttcggat | agaagacgtg | ttagagaatg | ttattgtttc | 1320 |
| ggaatggaga | ctttgttgaa | gcttgatttg | gaaggtacta | ggagattgtt | tgatgctttc | 1380 |
| tttgatgttg | atcccaagta | ctggcacggg | ttcctttctt | caagattgtc | tgtcaaagaa | 1440 |
| cttgctgtac | tcagtttgta | ccttttgga | catgcctcta | atttggctag | gttggatatt | 1500 |
| gttacaaagt | gcactgtccc | cttggttaaa | ctgctgggca | atctagcaat | agagagcctt | 1560 |
| tgaattaata | tgatagttt | gaagcactgt | tttcattta | atttcttagg | ttattttcat | 1620 |
| cttttctcaa | tgcaaaagtg | aaacaaaagc | tatacacatt | gtcatcgttg | ttcaaactca | 1680 |
| gacaagtttg | cctagctcta | tgtatttatc | cttaacatat | gtattcatca | aattcgaaat | 1740 |
| atacaatgca | ttggac | | | | | 1756 |

<210> SEQ ID NO 2
<211> LENGTH: 1497
<212> TYPE: DNA
<213> ORGANISM: Capsicum annuum

<400> SEQUENCE: 2
atggaaaccc ttctaaagcc ttttccatct cctttacttt ccattcctac tcctaacatg     60

```
tatagtttca aacacaactc cactttccca aatccaacca aacaaaaaga ttcaagaaag    120
ttccattata gaaacaaaag cagtacacat ttttgtagct ttcttgattt agcacccaca    180
tcaaagccag agtctttaga tgttaacatc tcatgggttg atactgatct ggacggggct    240
gaattcgacg tgatcatcat tggaactggc cctgccgggc ttcggctagc tgaacaagtt    300
tctaaatatg gtattaaggt atgttgcgtt gacccttcac cactttccat gtggccaaat    360
aattatggtg tttgggttga tgagtttgaa aagttgggat tagaagattg tctagatcat    420
aagtggcctg tgagttgtgt tcatataagt gatcacaaga ctaagtattt ggacagacca    480
tatggtagag taagtagaaa gaagttgaag ttgaaattgt tgaatagttg tgttgaaaat    540
agagtgaagt tttataaagc caaggttttg aaagtgaagc atgaagaatt tgagtcttcg    600 attgttgtg atgatggtag gaagataagc ggtagcttga ttgttgatgc aagtggctat    660
gctagtgatt ttatagagta tgacaagcca agaaaccatg gttatcaagt tgctcatggg    720
attttagcag aagttgataa tcatccattt gatttggata aaatgatgct tatggattgg    780
agggattctc atttaggtaa tgagccatat ctgagggtga agaatactaa agaaccaaca    840
ttcttgtatg caatgccatt tgataggaat ttggtattct tggaagagac ttctttagtg    900
agtcggccta tgttatcgta tatggaagtg aaaagaagga tggtagcaag attaagacat    960
ttggggatca aagtgagaag tgtccttgag gaagagaagt gtgtgatcac tatgggagga    1020
ccacttccgc ggattcctca aaatgttatg gctattggtg ggacttcagg gatagttcat    1080
ccatcgtctg ggtacatggt ggctcgtagc atggcattgg caccagtact ggctgaggcc    1140
atcgtcgaaa gccttggctc aacaagaatg ataagagggt ctcaactta ccatagagtt    1200 tggaatggtt tgtggccttc ggatagaaga cgtgttagag aatgttattg tttcggaatg    1260
gagactttgt tgaagcttga tttggaaggt actaggagat tgtttgatgc tttcttgat    1320 gttgatccca agtactggca cgggttcctt tcttcaagat tgtctgtcaa agaacttgct    1380
gtactcagtt tgtacctttt tggacatgcc tctaatttgg ctaggttgga tattgttaca    1440
aagtgcactg tccccttggt taaactgctg ggcaatctag caatagagag cctttga    1497
```

<210> SEQ ID NO 3
<211> LENGTH: 498
<212> TYPE: PRT
<213> ORGANISM: Capsicum annuum

<400> SEQUENCE: 3

```
Met Glu Thr Leu Leu Lys Pro Phe Pro Ser Pro Leu Leu Ser Ile Pro
1               5                   10                  15

Thr Pro Asn Met Tyr Ser Phe Lys His Asn Ser Thr Phe Pro Asn Pro
            20                  25                  30

Thr Lys Gln Lys Asp Ser Arg Lys Phe His Tyr Arg Asn Lys Ser Ser
        35                  40                  45

Thr His Phe Cys Ser Phe Leu Asp Leu Ala Pro Thr Ser Lys Pro Glu
    50                  55                  60

Ser Leu Asp Val Asn Ile Ser Trp Val Asp Thr Asp Leu Asp Gly Ala
65                  70                  75                  80

Glu Phe Asp Val Ile Ile Ile Gly Thr Gly Pro Ala Gly Leu Arg Leu
                85                  90                  95

Ala Glu Gln Val Ser Lys Tyr Gly Ile Lys Val Cys Cys Val Asp Pro
            100                 105                 110

Ser Pro Leu Ser Met Trp Pro Asn Asn Tyr Gly Val Trp Val Asp Glu
```

|  |  |  |  | 115 |  |  |  |  | 120 |  |  |  |  | 125 |  |  |
|--|--|--|--|--|--|--|--|--|--|--|--|--|--|--|--|--|

Phe Glu Lys Leu Gly Leu Glu Asp Cys Leu Asp His Lys Trp Pro Val
130                 135                 140

Ser Cys Val His Ile Ser Asp His Lys Thr Lys Tyr Leu Asp Arg Pro
145                 150                 155                 160

Tyr Gly Arg Val Ser Arg Lys Lys Leu Lys Leu Lys Leu Leu Asn Ser
                165                 170                 175

Cys Val Glu Asn Arg Val Lys Phe Tyr Lys Ala Lys Val Leu Lys Val
            180                 185                 190

Lys His Glu Glu Phe Glu Ser Ser Ile Val Cys Asp Asp Gly Arg Lys
        195                 200                 205

Ile Ser Gly Ser Leu Ile Val Asp Ala Ser Gly Tyr Ala Ser Asp Phe
210                 215                 220

Ile Glu Tyr Asp Lys Pro Arg Asn His Gly Tyr Gln Val Ala His Gly
225                 230                 235                 240

Ile Leu Ala Glu Val Asp Asn His Pro Phe Asp Leu Asp Lys Met Met
                245                 250                 255

Leu Met Asp Trp Arg Asp Ser His Leu Gly Asn Glu Pro Tyr Leu Arg
            260                 265                 270

Val Lys Asn Thr Lys Glu Pro Thr Phe Leu Tyr Ala Met Pro Phe Asp
        275                 280                 285

Arg Asn Leu Val Phe Leu Glu Glu Thr Ser Leu Val Ser Arg Pro Met
290                 295                 300

Leu Ser Tyr Met Glu Val Lys Arg Arg Met Val Ala Arg Leu Arg His
305                 310                 315                 320

Leu Gly Ile Lys Val Arg Ser Val Leu Glu Glu Lys Cys Val Ile
                325                 330                 335

Thr Met Gly Gly Pro Leu Pro Arg Ile Pro Gln Asn Val Met Ala Ile
            340                 345                 350

Gly Gly Thr Ser Gly Ile Val His Pro Ser Ser Gly Tyr Met Val Ala
        355                 360                 365

Arg Ser Met Ala Leu Ala Pro Val Leu Ala Glu Ala Ile Val Glu Ser
370                 375                 380

Leu Gly Ser Thr Arg Met Ile Arg Gly Ser Gln Leu Tyr His Arg Val
385                 390                 395                 400

Trp Asn Gly Leu Trp Pro Ser Asp Arg Arg Val Arg Glu Cys Tyr
                405                 410                 415

Cys Phe Gly Met Glu Thr Leu Leu Lys Leu Asp Leu Glu Gly Thr Arg
            420                 425                 430

Arg Leu Phe Asp Ala Phe Phe Asp Val Asp Pro Lys Tyr Trp His Gly
        435                 440                 445

Phe Leu Ser Ser Arg Leu Ser Val Lys Glu Leu Ala Val Leu Ser Leu
450                 455                 460

Tyr Leu Phe Gly His Ala Ser Asn Leu Ala Arg Leu Asp Ile Val Thr
465                 470                 475                 480

Lys Cys Thr Val Pro Leu Val Lys Leu Leu Gly Asn Leu Ala Ile Glu
                485                 490                 495

Ser Leu

<210> SEQ ID NO 4
<211> LENGTH: 136
<212> TYPE: DNA
<213> ORGANISM: Capsicum annuum

```
<400> SEQUENCE: 4
tctagcaata gagagccttt gaattaatat gatagttttg aagcactgtt ttcattttaa          60
tttcttaggt tattttcatc ttttctcaat gcaaaagtga aacaaaagct atacacattg        120
tcatcgttgt tcaaac                                                        136

<210> SEQ ID NO 5
<211> LENGTH: 136
<212> TYPE: DNA
<213> ORGANISM: Capsicum annuum

<400> SEQUENCE: 5
tctagcaata gagagccttt gaattaatat gatagttttg aagcactgct ttcattttaa          60
tttcttaggt tattttcatc ttttatcaat gcaaaagtga aacaaaagct atacacattg        120
tcatcgttgt tcaaac                                                        136
```